United States Patent
Wu et al.

(10) Patent No.: US 11,459,549 B2
(45) Date of Patent: Oct. 4, 2022

(54) METHOD FOR BIOCATALYTIC SYNTHESIS OF SITAGLIPTIN AND INTERMEDIATE THEREOF

(71) Applicants: China Fortune Way Company, Beijing (CN); Nanjing Redwood Fine Chemical Co., Ltd, Jiangsu (CN)

(72) Inventors: Fahao Wu, Nanjing (CN); Wen Yang, Beijing (CN); Gang Li, Nanjing (CN); Hongwei Shi, Beijing (CN); Yangzhe Gao, Nanjing (CN); Lili Liu, Beijing (CN); Zhifa Yuan, Beijing (CN)

(73) Assignees: China Fortune Way Company, Beijing (CN); Nanjing Redwood Fine Chemical Co., Ltd., Nanjing (CN)

(*) Notice: Subject to any disclaimer, the term of this patent is extended or adjusted under 35 U.S.C. 154(b) by 0 days.

(21) Appl. No.: 17/054,135

(22) PCT Filed: Jul. 27, 2018

(86) PCT No.: PCT/CN2018/097354
§ 371 (c)(1),
(2) Date: Nov. 9, 2020

(87) PCT Pub. No.: WO2019/214084
PCT Pub. Date: Nov. 14, 2019

(65) Prior Publication Data
US 2021/0123080 A1    Apr. 29, 2021

(30) Foreign Application Priority Data
May 10, 2018 (CN) .......................... 201810442572.3

(51) Int. Cl.
*C12N 9/10* (2006.01)
*C12P 13/00* (2006.01)
*C07D 295/182* (2006.01)

(52) U.S. Cl.
CPC ....... *C12N 9/1096* (2013.01); *C07D 295/182* (2013.01); *C12P 13/001* (2013.01)

(58) Field of Classification Search
CPC .............................. C12N 9/1096; C12P 13/001
See application file for complete search history.

(56) References Cited

U.S. PATENT DOCUMENTS

| | | | |
|---|---|---|---|
| 8,293,507 B2 | 10/2012 | Savile et al. | |
| 2003/0100563 A1 | 5/2003 | Edmondson et al. | |
| 2009/0156579 A1 | 6/2009 | Hasegawa | |
| 2013/0260426 A1 | 10/2013 | Ang et al. | |
| 2017/0073651 A1 | 3/2017 | Dhawan et al. | |

FOREIGN PATENT DOCUMENTS

| | | |
|---|---|---|
| CN | 102093245 A | 6/2011 |
| CN | 102277322 A | 12/2011 |
| CN | 102405281 A | 4/2012 |
| CN | 102485718 A | 6/2012 |
| CN | 102574856 A | 7/2012 |
| CN | 102574862 A | 7/2012 |
| CN | 102597226 A | 7/2012 |
| CN | 102702205 A | 10/2012 |
| CN | 103014081 A | 4/2013 |
| CN | 104805069 A | 7/2015 |
| CN | 104893989 A | 9/2015 |
| CN | 105018440 A | 11/2015 |
| CN | 105274027 A | 1/2016 |
| CN | 105294479 A | 2/2016 |
| CN | 105331651 A | 2/2016 |
| CN | 106191148 A | 12/2016 |
| CN | 106748888 A | 5/2017 |
| CN | 106801043 A | 6/2017 |
| CN | 106995808 A | 8/2017 |
| CN | 107286164 A | 10/2017 |
| CN | 107365809 A | 11/2017 |
| CN | 107384887 A | 11/2017 |
| CN | 109234327 A | 1/2019 |
| WO | 2009/064476 A1 | 5/2009 |
| WO | 2010/081053 A2 | 7/2010 |
| WO | 2010/099501 A2 | 9/2010 |
| WO | 2011/005477 A1 | 1/2011 |
| WO | 2011/049344 A2 | 4/2011 |

(Continued)

OTHER PUBLICATIONS

Studer. Residue mutations and their impact on protein structure and function: detecting beneficial and pathogenic changes. Biochem. J. (2013) 449, 581-594.*

(Continued)

*Primary Examiner* — Yong D Pak
(74) *Attorney, Agent, or Firm* — Christenson O'Connor Johnson Kindness PLLC

(57) ABSTRACT

Provided is a method for biocatalytic synthesis of Sitagliptin and intermediates thereof, in particular, provided are compounds of Formula (I) and Formula (II), or pharmaceutically acceptable salts thereof, a polypeptide capable of catalyzing conversion of a compound of Formula (I) to a compound of Formula (II), a nucleic acid encoding the polypeptide, a vector and a cell comprising the nucleic acid. In addition, also provided are a method for producing a compound of Formula (II) and Sitagliptin by using the polypeptide and the compound of Formula (I), and a method for preparing the polypeptide.

19 Claims, 10 Drawing Sheets
Specification includes a Sequence Listing.

(56) References Cited

FOREIGN PATENT DOCUMENTS

WO 2011/135586 A2 11/2011

OTHER PUBLICATIONS

Xu, F., et al., "Mechanistic Evidence for an α-Oxoketene Pathway in the Formation of β-Ketoamides/Esters via Meldrum's Acid Adducts," Journal of the American Chemical Society 126(40):13002-13009, Sep. 2004.
International Search Report and Written Opinion dated Feb. 12, 2019, issued in corresponding International Application No. PCT/CN2018/097354 filed Jul. 27, 2018, 13 pages.
Savile, K., et al., "Biocatalytic Asymmetric Synthesis of Chiral Amines from Ketones Applied to Sitagliptin Manufacture," Science, vol. 329:305-309, Jul. 2010.

* cited by examiner

METHOD FOR BIOCATALYTIC SYNTHESIS OF SITAGLIPTIN AND INTERMEDIATE THEREOF

CROSS-REFERENCES TO RELATED APPLICATIONS

This application is a National Stage of Application No. PCT/CN2018/097354, filed Jul. 27, 2018, which claims the benefit of Chinese Application No. 20180442572.3, filed May 10, 2018, the entire disclosure of each of which is hereby incorporated by reference herein for all purposes.

STATEMENT REGARDING SEQUENCE LISTING

The sequence listing associated with this application is provided in text format in lieu of a paper copy and is hereby incorporated by reference into the specification. The name of the text file containing the sequence listing is 73134_Seq.txt. The text file is 19 KB and is being submitted via EFS-Web with the filing of the specification.

TECHNICAL FIELD

The present application relates to the technical field of molecular biology, particularly relates to the field of biosynthesis of Sitagliptin. In particular, the present application provides compounds of Formula I and Formula II or pharmaceutically acceptable salts thereof, a polypeptide effective in carrying out catalytic conversion of compound of Formula I to a compound of Formula II, a nucleic acid encoding the polypeptide, a vector and a cell comprising the nucleic acid. In addition, the present application also provides a method for producing the compound of Formula II and Sitagliptin by using the polypeptide and the compound of Formula I, and a method for preparing the polypeptide.

BACKGROUND ART

Sitagliptin (the structure of which is shown below), the chemical name of which is (3R)-3-amino-1-[3-(trifluoromethyl)-5,6,7,8-tetrahydro-1,2,4-triazolo[4,3-a]pyrazin-7-yl]-4-(2,4,5-trifluorophenyl)butan-1-one, is an oral anti-diabetic drug. It can be applied alone or in combination with other oral antidiabetic drug(s) (such as metformin or thiazolidinedione) in treating Type 2 Diabetes. As compared with other oral antidiabetic drug, Sitagliptin has less side effects in controlling blood glucose level (i.e. is less likely to cause hypoglycemia or body weight gain).

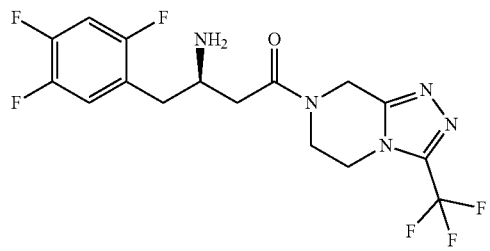 [SMILES: N[C@@H](CC(=O)N1CCn2c(nnc2C(F)(F)F)C1)Cc1cc(F)c(F)cc1F]

Sitagliptin

Sitagliptin has a chiral center in its structure, and the construction of the chiral center is the key step for the synthesis of Sitagliptin. Methods for constructing the chiral center in current research mainly includes: (1) asymmetric hydrogenation of a corresponding enamine substrate in the presence of a chiral catalyst; (2) using a chiral amine compound as a starting material; (3) chiral resolution; and (4) converting from a β-carbonyl ester compound by using a transaminase as catalyst. The above mentioned methods, however, provide high cost, poor enantioselectivity, difficulty in workup, and poor yield of product.

In recent years, bio-enzyme catalysis gradually become the preferred solutions for the synthesis of chiral pharmaceutical chemicals and intermediates thereof due to its high selectivity and environment friendliness.

Transaminase, also called aminotransferase, is a key enzyme for asymmetric synthesis of chiral amines with high optical purity, and is widely distributed in plants, animals and microorganisms. As so far, many ω-transaminase genes have been cloned, some of which have been expressed in different hosts (*E. coli, Pichia pastoris*, etc.). Bacteria capable of producing ω-Transaminase with high activity and selectivity are gained. ω-Transaminase now is also used in the production of Sitagliptin. However, there are few reports about naturally occurring ω-transaminase for (R)-selective transamination. Furthermore, the ω-transaminase is often an optimal catalyst screened for a specific reaction and generally has a narrow profile of substrates.

Therefore, searching for methods, especially bio-catalytic methods of constructing the chiral center of Sitagliptin provides new options for solving the problem confronted in the synthesis of the drug.

SUMMARY

In one aspect, the present disclosure features a compound of Formula I, or a pharmaceutically acceptable salt thereof.

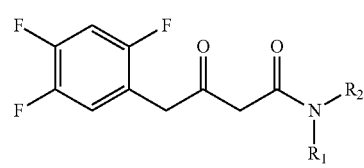

I wherein, $R_1$ and $R_2$ are independently selected from the group consisting of hydrogen, $C_{1-6}$alkyl, 3-8-membered cycloalkyl, 3-8-membered heterocyclic alkyl, 6-10-membered aryl and 5-10-membered heteroaryl; or, $R_1$ and $R_2$ together with the N atom to which they are linked form a 4-7-membered heterocycle;

preferably, $R_1$ and $R_2$ are independently selected from the group consisting of hydrogen, $C_{1-4}$alkyl, 3-6-membered cycloalkyl, 3-6-membered heterocyclic alkyl, 6-10-membered aryl and 5-6-membered heteroaryl; or, $R_1$ and $R_2$ together with the N atom to which they are linked form a 5-6-membered aliphatic heterocycle or a 5-6-membered aromatic heterocycle;

preferably, $R_1$ and $R_2$ are independently selected from the group consisting of hydrogen and $C_{1-4}$alkyl; or, $R_1$ and $R_2$ together with the N atom to which they are linked form a 5-6-membered aliphatic heterocycle or a 5-6-membered aromatic heterocycle;

preferably, $R_1$ and $R_2$ together with the N atom to which they are linked form a pyrrole ring, an imidazole ring, a pyrrolidine ring, an oxazolidine ring, an isoxazolidine ring, a piperidine ring, a morpholine ring or a piperazine ring;

preferably, $R_1$ and $R_2$ together with the N atom to which they are linked form a morpholine ring.

In another aspect, the present disclosure features a compound of Formula II, or a pharmaceutically acceptable salt thereof,

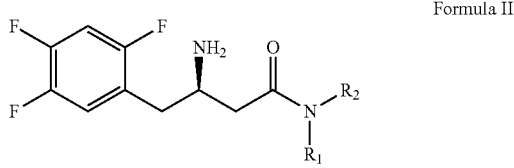

Formula II wherein, $R_1$ and $R_2$ are independently selected from the group consisting of hydrogen, $C_{1-6}$alkyl, 3-8-membered cycloalkyl, 3-8-membered heterocyclic alkyl, 6-10-membered aryl and 5-10-membered heteroaryl; or, $R_1$ and $R_2$ together with the N atom to which they are linked form a 4-7-membered heterocycle;

preferably, $R_1$ and $R_2$ are independently selected from the group consisting of hydrogen, $C_{1-4}$alkyl, 3-6-membered cycloalkyl, 3-6-membered heterocyclic alkyl, 6-10-membered aryl and 5-6-membered heteroaryl; or, $R_1$ and $R_2$ together with the N atom to which they are linked form a 5-6-membered aliphatic heterocycle or a 5-6-membered aromatic heterocycle;

preferably, $R_1$ and $R_2$ are independently selected from the group consisting of hydrogen and $C_{1-4}$alkyl; or, $R_1$ and $R_2$ together with the N atom to which they are linked form a 5-6-membered aliphatic heterocycle or a 5-6-membered aromatic heterocycle;

preferably, $R_1$ and $R_2$ together with the N atom to which they are linked form a pyrrole ring, an imidazole ring, a pyrrolidine ring, an oxazolidine ring, an isoxazolidine ring, a piperidine ring, a morpholine ring or a piperazine ring;

preferably, $R_1$ and $R_2$ together with the N atom to which they are linked form a morpholine ring.

In yet another aspect, the present disclosure features a polypeptide having the activity of catalyzing the conversion of a carbonyl group to an amino group, and having an amino acid sequence selected from the group consisting of:

1) an amino acid sequence set forth in SEQ ID NO: 1;

2) an amino acid sequence having at least 90%, 91%, 92%, 93%, 94%, 95%, 96%, 97%, 98%, or 99% sequence identity to SEQ ID NO: 1; and (3) an amino acid sequence that differs from SEQ ID NO: 1 by substitution, deletion or addition of one or more (e.g. 1, 2, 3, 4, 5, 6, 7, 8 or 9) amino acid residues.

In yet another aspect, the present disclosure features a method for producing a compound of Formula II or a pharmaceutically acceptable salt thereof, comprising the step of converting a compound of Formula I to a compound of Formula II by using the polypeptide described above or the composition described above, wherein, the compound of Formula I or a pharmaceutically acceptable salt thereof has the same meanings as defined above;

the compound of Formula II or a pharmaceutically acceptable salt thereof has the same meanings as defined above;

preferably, the method comprises (a) reacting the compound of Formula I with an amino donor in the presence of the polypeptide or the composition and an amino transmitter; and (b) collecting the compound of Formula II produced in the step (a);

more preferably, in the step (a), $V(ml)_{the\ composition}$: $m(g)_{the\ compound\ of\ Formula\ I}=(2-5):1$; more preferably, the polypeptide is used in an amount of 10 wt. %-80 wt. % of the compound of Formula I; in the step (a), the amino donor is selected from $C_{1-6}$alkylamine (e.g. isopropyl amine) and an inorganic ammonium salt (e.g. ammonium formate, ammonium chloride or ammonium sulfate), and isopropyl amine is more preferred; preferably, the molar ratio of the compound of Formula I to the amino donor is 1: (1-3) (e.g. 1: (1.2-3)); preferably, in the step (a), the amino transmitter is selected from pyridoxal phosphate and pyridoxamine phosphate; preferably, in the step (a), the reaction is carried out in an aqueous phase, more preferably, the compound of Formula I is dissolved in an alcohol solvent (e.g. methanol, ethanol or isopropanol) before being added to a reaction system (e.g. the compound of Formula I is dissolved in an alcohol solvent to form a 1-5 Kg/L solution, e.g. 1-4 Kg/L, e.g. 3-4 Kg/L); preferably, the concentration of the compound of Formula I is 100 g/L-250 g/L in the reaction system; preferably, in the step (a), the reaction is carried out at 30-50° C. (preferably 45° C.); preferably, in the step (a), the reaction system has a pH of 7.0-9.0 (preferably 8.0-9.0), more preferably, an organic amine (e.g. isopropyl amine, butyl amine or pentyl amine) is used to adjust pH of the reaction system; preferably, in the step (a), the reaction system is in contact with air;

more preferably, in the step (b), the compound of Formula II is collected by the following method: the product obtained in the step (a) is extracted with an organic solvent and concentrated; more preferably, the organic solvent is selected from the group consisting of dichloromethane, ethyl acetate and isopropyl acetate.

In yet a further aspect, the present disclosure features a method for synthesizing Sitagliptin or a salt thereof, comprising the following steps:

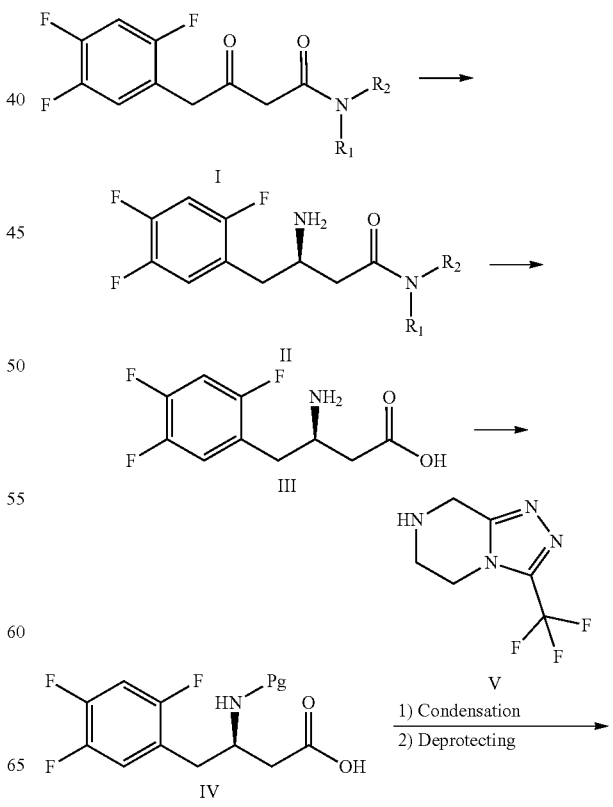

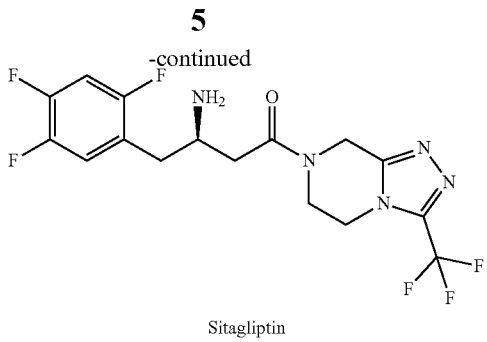

Sitagliptin the first step: a compound of Formula I is subjected to an asymmetric catalytic reaction to produce a compound of Formula II;

the second step: the compound of Formula II is hydrolyzed in the presence of a base to produce a compound of Formula III;

the third step: the amino group in the compound of Formula III is protected to produce a compound of Formula IV; and the fourth step: the compound of Formula IV and a compound of Formula V are subjected to condensation reaction, and the amino-protecting group of the product is removed, to produce Sitagliptin or a salt thereof;

wherein, -Pg represents an amino-protecting group, e.g. Boc, Cbz, Fmoc or Alloc;

$R_1$ and $R_2$ have the same meanings as defined above.

DETAILED DESCRIPTION

Contents of Invention

A non-naturally occurring enzyme is obtained by mutation of the gene sequence of wild-type transaminase from *Arthrobacter*. The enzyme is capable of stereospecifically catalyzing β-carbonyl amide to produce (R)-chiral amine. Based on this, the inventor develop a new method for synthesis of Sitagliptin.

Therefore, in an aspect, the present application provides a key intermediate for constructing the chiral center of Sitagliptin, which is a β-carbonyl amide compound, can be used as a substrate of the enzyme, and can be converted stereospecifically to (R)-amine. The intermediate for constructing the chiral center of Sitagliptin is a compound of Formula I, or a pharmaceutically acceptable salt thereof,

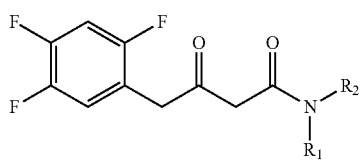

I wherein, $R_1$ and $R_2$ are independently selected from the group consisting of hydrogen, $C_{1-6}$alkyl, 3-8-membered cycloalkyl, 3-8-membered heterocyclic alkyl, 6-10-membered aryl and 5-10-membered heteroaryl; or, $R_1$ and $R_2$ together with the N atom to which they are linked form a 4-7-membered heterocycle.

In some preferred embodiments, $R_1$ and $R_2$ are independently selected from the group consisting of hydrogen, $C_{1-4}$alkyl, 3-6-membered cycloalkyl, 3-6-membered heterocyclic alkyl, 6-10-membered aryl and 5-6-membered heteroaryl; or, $R_1$ and $R_2$ together with the N atom to which they are linked form a 5-6-membered aliphatic heterocycle or a 5-6-membered aromatic heterocycle.

In some preferred embodiments, $R_1$ and $R_2$ are independently selected from the group consisting of hydrogen and $C_{1-4}$ alkyl; or, $R_1$ and $R_2$ together with the N atom to which they are linked form a 5-6-membered aliphatic heterocycle or a 5-6-membered aromatic heterocycle.

In some preferred embodiments, $R_1$ and $R_2$ together with the N atom to which they are linked form a pyrrole ring, an imidazole ring, a pyrrolidine ring, an oxazolidine ring, an isoxazolidine ring, a piperidine ring, a morpholine ring or a piperazine ring.

In some preferred embodiments, $R_1$ and $R_2$ together with the N atom to which they are linked form a pyrrole ring.

In some preferred embodiments, $R_1$ and $R_2$ together with the N atom to which they are linked form an imidazole ring.

In some preferred embodiments, $R_1$ and $R_2$ together with the N atom to which they are linked form a pyrrolidine ring.

In some preferred embodiments, $R_1$ and $R_2$ together with the N atom to which they are linked form an oxazolidine ring.

In some preferred embodiments, $R_1$ and $R_2$ together with the N atom to which they are linked form an isoxazolidine ring.

In some preferred embodiments, $R_1$ and $R_2$ together with the N atom to which they are linked form a piperidine ring.

In some preferred embodiments, $R_1$ and $R_2$ together with the N atom to which they are linked form a morpholine ring.

In some preferred embodiments, $R_1$ and $R_2$ together with the N atom to which they are linked form a piperazine ring.

In another aspect, the present application provides the chiral intermediate of Sitagliptin, a compound of Formula II, or a pharmaceutically acceptable salt thereof, Formula II

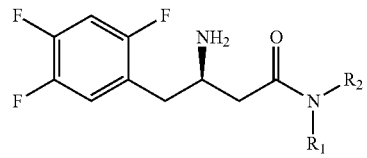

wherein, $R_1$ and $R_2$ are independently selected from the group consisting of hydrogen, $C_{1-6}$alkyl, 3-8-membered cycloalkyl, 3-8-membered heterocyclic alkyl, 6-10-membered aryl and 5-10-membered heteroaryl; or, $R_1$ and $R_2$ together with the N atom to which they are linked form a 4-7-membered heterocycle.

In some preferred embodiments, $R_1$ and $R_2$ are independently selected from the group consisting of hydrogen, $C_{1-4}$alkyl, 3-6-membered cycloalkyl, 3-6-membered heterocyclic alkyl, 6-10-membered aryl and 5-6-membered heteroaryl; or, $R_1$ and $R_2$ together with the N atom to which they are linked form a 5-6-membered aliphatic heterocycle or a 5-6-membered aromatic heterocycle.

In some preferred embodiments, $R_1$ and $R_2$ are independently selected from the group consisting of hydrogen and $C_{1-4}$alkyl; or, $R_1$ and $R_2$ together with the N atom to which they are linked form a 5-6-membered aliphatic heterocycle or a 5-6-membered aromatic heterocycle.

In some preferred embodiments, $R_1$ and $R_2$ together with the N atom to which they are linked form a pyrrole ring, an imidazole ring, a pyrrolidine ring, an oxazolidine ring, an isoxazolidine ring, a piperidine ring, a morpholine ring or a piperazine ring.

In some preferred embodiments, $R_1$ and $R_2$ together with the N atom to which they are linked form a pyrrole ring.

In some preferred embodiments, $R_1$ and $R_2$ together with the N atom to which they are linked form an imidazole ring.

In some preferred embodiments, $R_1$ and $R_2$ together with the N atom to which they are linked form a pyrrolidine ring.

In some preferred embodiments, $R_1$ and $R_2$ together with the N atom to which they are linked form an oxazolidine ring.

In some preferred embodiments, $R_1$ and $R_2$ together with the N atom to which they are linked form an isoxazolidine ring.

In some preferred embodiments, $R_1$ and $R_2$ together with the N atom to which they are linked form a piperidine ring.

In some preferred embodiments, $R_1$ and $R_2$ together with the N atom to which they are linked form a morpholine ring.

In some preferred embodiments, $R_1$ and $R_2$ together with the N atom to which they are linked form a piperazine ring.

In another aspect, the present application provides a polypeptide having the activity of catalyzing the conversion of a carbonyl group to an amino group, and having an amino acid sequence selected from the group consisting of:

1) an amino acid sequence set forth in SEQ ID NO: 1;
2) an amino acid sequence having at least 90% sequence identity to SEQ ID NO: 1; and
3) an amino acid sequence that differs from SEQ ID NO: 1 by substitution, deletion or addition of one or more amino acid residues.

In some preferred embodiments, the amino acid sequence of the polypeptide according to the present application has at least 90%, 91%, 92%, 93%, 94%, 95%, 96%, 97%, 98%, or 99% sequence identity to SEQ ID NO: 1.

In some preferred embodiments, the amino acid sequence of the polypeptide according to the present application differs from SEQ ID NO: 1 by substitution, deletion or addition of one or more (e.g. 1, 2, 3, 4, 5, 6, 7, 8 or 9) amino acid residues.

In some preferred embodiments, the polypeptide according to the present application has the activity of catalyzing a compound of Formula I to produce a compound of Formula II, wherein the compound of Formula I and the compound of Formula II have the same meanings as defined above.

In another aspect, the present application provides an isolated nucleic acid encoding the polypeptide as described above.

In another aspect, the present application further provides a vector comprising the isolated nucleic acid. In some preferred embodiments, the isolated nucleic acid according to the present application encodes the polypeptide having an amino acid sequence of SEQ ID NO: 1. Vectors for insertion of a target nucleotide are well known in the art, including, but not limited to a cloning vector and an expression vector. In an embodiment, the vector may be a plasmid, a cosmid, a phage, etc.

In another aspect, the present application further provides a host cell comprising the isolated nucleic acid and/or the vector. Such host cells include, but are not limited to, a prokaryotic cell such as *E. coli* cell or *Bacillus* cell (e.g., *Bacillus basophilus*, *Bacillus subtilis*), and an eukaryotic cell such as a yeast cell, an insect cell, a plant cell and an animal cell. In some preferred embodiments, the isolated nucleic acid is heterogenous or exogenous for the cell.

In another aspect, the present application further provides a composition comprising the polypeptide as described above.

In some preferred embodiments, the composition is prepared by the following method:

(a) culturing a host cell comprising and expressing the nucleic acid encoding the polypeptide as described above;
(b) collecting and disrupting the host cell, to obtain a cell disrupting solution; (c) filtrating the cell disrupting solution; and (d) collecting the filtrate; optionally, a process of diluting the filtrate with a pH 8.0 PBS is further comprised.

In some preferred embodiments, the host cell is collected by centrifugation or membrane filtration; preferably, after the host cell is collected by centrifugation or membrane filtration, the method further comprises a process of washing the host cell with a phosphate buffer. In some preferred embodiments, the host cell is disrupted by an ultrasonic disrupter or a high pressure homogenizer. In some preferred embodiments, the cell disrupting solution is subjected to centrifugation before filtration. In some preferred embodiments, the composition comprises 10 wt. %-20 wt. % of the polypeptide, e.g. 10 wt. %, 11 wt. %, 12 wt. %, 13 wt. %, 14 wt. %, 15 wt. %, 16 wt. %, 17 wt. %, 18 wt. %, 19 wt. %, or 20 wt. %.

In another aspect, the present application provides a method for producing the compound of Formula II or the pharmaceutically acceptable salt thereof, comprising the step of converting a compound of Formula I to a compound of Formula II by using the polypeptide or the composition as described above, wherein, the compounds of Formula I and Formula II or pharmaceutically acceptable salts thereof have the same meanings as defined above.

In some preferred embodiments, the method comprises (a) reacting the compound of Formula I with an amino donor in the presence of the polypeptide or the composition and an amino transmitter; and (b) collecting the compound of Formula II produced in the step (a).

The amount of the catalyst can be determined by conventional technical means in the art. In some preferred embodiments, in the step (a), $V(ml)_{the\ composition}$ : $m(g)_{the\ compound\ of\ Formula\ I}$ =(2-5): 1, e.g. (4-5):1, 2:1, 2.5:1, 3:1, 3.5:1, 4:1, 4.5:1, or 5:1. In some preferred embodiments, the polypeptide is used in an amount of 10 wt. %-80 wt. % of the compound of Formula I, e.g. 10 wt. %, 20 wt. %, 30 wt. %, 40 wt. %, 50 wt. %, 60 wt. %, 70 wt. %, or 80 wt. %.

In some preferred embodiments, in the step (a), the amino donor is selected from $C_{1-6}$alkylamine and an inorganic ammonium salt. In some preferred embodiments, the $C_{1-6}$alkylamine is isopropyl amine. In some preferred embodiments, the inorganic ammonium salt is selected from the group consisting of ammonium formate, ammonium chloride and ammonium sulfate. In some preferred embodiments, the amino donor is isopropyl amine. In some preferred embodiments, the molar ratio of the compound of Formula I to the amino donor is 1: (1-3). In some preferred embodiments, the molar ratio of the compound of Formula I to the amino donor is 1: (1.2-3).

In some preferred embodiments, in the step (a), the amino transmitter is selected from pyridoxal phosphate and pyridoxamine phosphate.

In some preferred embodiments, in the step (a), the reaction is carried out in an aqueous phase. In some preferred embodiments, the compound of Formula I is dissolved in an alcohol solvent before being added to a reaction system. In some preferred embodiments, the compound of Formula I may be dissolved in an alcohol solvent to form a 1-5 Kg/L solution, e.g. 1-4 Kg/L, e.g. 3-4 Kg/L. In some preferred embodiments, the alcohol solvent is selected from the group consisting of methanol, ethanol and isopropanol.

In some preferred embodiments, in the reaction system, the concentration of the compound of Formula I is 100-250 g/L.

In some preferred embodiments, in the step (a), the reaction is carried out at 30-50° C. In some preferred embodiments, in the step (a), the reaction is carried out at 45° C.

In some preferred embodiments, in the step (a), the pH of the reaction system is 7.0-9.0. In some preferred embodiments, the pH of the reaction system is 8.0-9.0. In some preferred embodiments, an organic amine is used to adjust the pH of the reaction system. In some preferred embodiments, the organic amine is selected from the group consisting of isopropyl amine, butyl amine and pentyl amine.

In some preferred embodiments, in the step (a), the reaction system is in contact with air.

In some preferred embodiments, in the step (b), the compound of Formula II is collected by the following method: the product obtained in the step (a) is extracted with an organic solvent, and concentrated. In some preferred embodiments, the organic solvent is selected from the group consisting of dichloromethane, ethyl acetate and isopropyl acetate.

In another aspect, the present application provides a method for synthesizing Sitagliptin or a salt thereof, comprising the following steps:

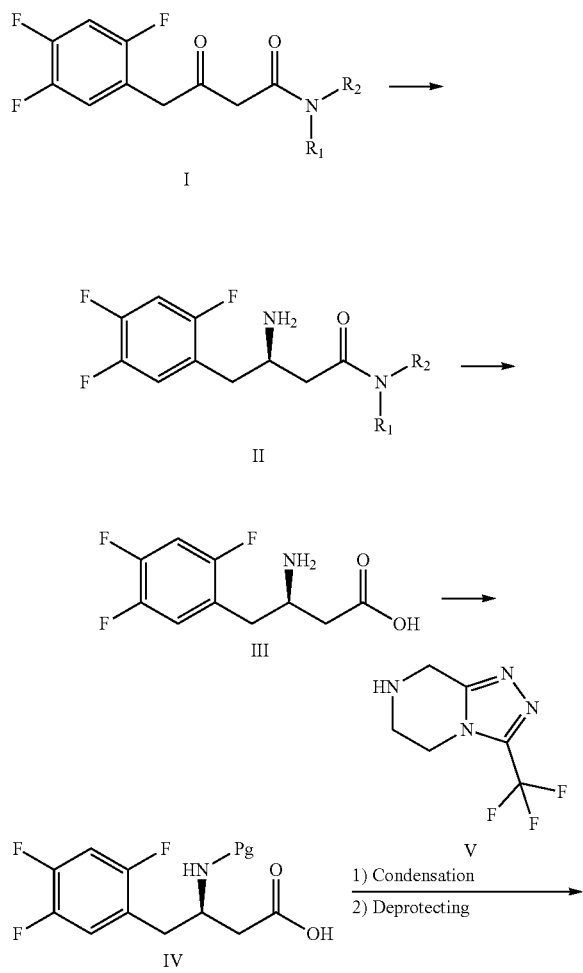

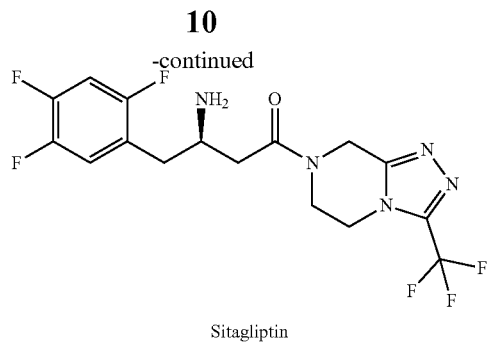

Sitagliptin the first step: a compound of Formula I is subjected to an asymmetric catalytic reaction to produce a compound of Formula II;

the second step: the compound of Formula II is hydrolyzed in the presence of a base to produce a compound of Formula III;

the third step: the amino group in the compound of Formula III is protected to produce a compound of Formula IV; and the fourth step: the compound of Formula IV and a compound of Formula V are subjected to condensation reaction, and the amino-protecting group of the product is removed, to produce Sitagliptin or a salt thereof;

wherein, -Pg represents an amino-protecting group, $R_1$ and $R_2$ have the same meanings as defined above.

In some preferred embodiments, the amino-protecting group is Boc, Cbz, Fmoc or Alloc.

In some preferred embodiments, the compound of Formula I may be produced by the following method:

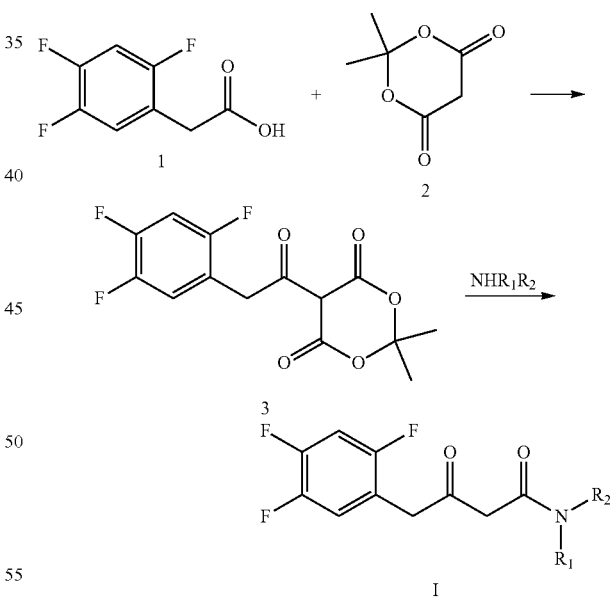

a) Compound 1 is reacted with Compound 2 in an aprotic solvent, in the presence of an organic base, at room temperature or under heating, to produce Compound 3; and b) Compound 3 is reacted with $NHR_1R_2$ in a non-alcohol solvent, under heating, to produce a compound of Formula I.

In some preferred embodiments, Compound 1 is reacted with Compound 2 in EtOAc, DCM, DMF, DMA or DMSO. In some preferred embodiments, Compound 1 is reacted with Compound 2 in DMA.

In some preferred embodiments, Compound 1 is reacted with Compound 2 in the presence of methylamine, triethylamine, n-butyl amine or tert-butyl amine. In some preferred embodiments, Compound 1 is reacted with Compound 2 in the presence of triethylamine.

In some preferred embodiments, Compound 1 is reacted with Compound 2 at 20-50° C. In some preferred embodiments, Compound 1 is reacted with Compound 2 at 35° C.

In some preferred embodiments, the molar ratio of Compound 1 to Compound 2 is 1: (1-5).

In some preferred embodiments, after the reaction of Compound 1 with Compound 2, the step of adding an acidification agent is further comprised. In some preferred embodiments, the acidification agent is selected from the group consisting of hydrochloric acid, thionyl chloride and pivaloyl chloride. In some preferred embodiments, the acidification agent is hydrochloric acid. In some preferred embodiments, the acidification agent is added in such an amount that the reaction system has an acidic pH.

In some preferred embodiments, Compound 3 is reacted with $NHR_1R_2$ in benzene, toluene or tetrahydronaphthalene.

In some preferred embodiments, the reaction of Compound 3 with $NHR_1R_2$ is catalyzed by an inorganic base. In some preferred embodiments, the inorganic base is sodium hydroxide or potassium hydroxide.

In some preferred embodiments, Compound 3 is reacted with $NHR_1R_2$ at 40-120° C. In some preferred embodiments, Compound 3 is reacted with $NHR_1R_2$ at 100-105° C.

In some preferred embodiments, the molar ratio of Compound 3 to $NHR_1R_2$ is 1: (2-4).

In some preferred embodiments, in the first step, the asymmetric catalytic reaction is an asymmetric reductive amination reaction. In some preferred embodiments, the catalyst for catalyzing the asymmetric reductive amination reaction is selected from the group consisting of chiral metal complex catalysts of rhodium, palladium and ruthenium. In some preferred embodiments, the chiral metal complex catalysts of rhodium, palladium and ruthenium are selected from the group consisting of dichlorobis(di-tert-butylphenylphosphine)palladium (II), (p-cymene)ruthenium and bis [rhodium($\alpha,\alpha,\alpha',\alpha'$-tetramethyl-1,3-benzenedipropionic acid)].

In some preferred embodiments, the catalyst used in the asymmetric catalytic reaction is the polypeptide or the composition as described above.

In some preferred embodiments, the reaction condition for asymmetrically catalyzing a compound of Formula I to produce a compound of Formula II is as defined above.

In some preferred embodiments, a compound of Formula II is hydrolyzed in the presence of an inorganic base to produce a compound of Formula III. In some preferred embodiments, the inorganic base is sodium hydroxide or potassium hydroxide.

In some preferred embodiments, Boc anhydride is reacted with a compound of Formula III in the presence of a base to protect the corresponding amino group. In some preferred embodiments, the molar ratio of the compound of Formula III, the Boc anhydride to the base is 1: (1.5-3): (2-4). In some preferred embodiments, the base is selected from the group consisting of sodium hydroxide, potassium hydroxide and triethylamine.

In some preferred embodiments, an active intermediate of the compound of Formula IV, and a compound of Formula V are subjected to the condensation reaction. In some preferred embodiments, the active intermediate of the compound of Formula IV is an acyl chloride, an anhydride or an amide thereof.

In some preferred embodiments, the molar ratio of the compound of Formula IV to the compound of Formula V is 1: (1-1.2).

In some preferred embodiments, the condensation reaction is carried out in a non-alcohol solvent. In some preferred embodiments, the non-alcohol solvent is ethyl acetate, dichloromethane or chloroform.

In some preferred embodiments, the condensation reaction is carried out at room temperature (e.g. 25° C.).

In some preferred embodiments, the condensation reaction is carried out in the presence of a base. In some preferred embodiments, the base is triethylamine.

In another aspect, the present application provides a method for preparing the polypeptide as described above, comprising (a) culturing a host cell comprising and expressing a nucleic acid encoding the polypeptide, and (b) collecting the polypeptide expressed in the cell.

A variety of host cells for protein expression are well known by a person skilled in the art, including, but not limited to, prokaryotic cells such as *E. coli* cell, and eukaryotic cells such as yeast cells, insect cells, plant cells and animal cells (for example, mammalian cells, e.g. mouse cells, human cells, etc.). A particularly preferred host cell is *E. coli*.

In another aspect, the present application provides use of the compound of Formula I or Formula II or the pharmaceutically acceptable salt thereof, the polypeptide, or the composition as described above in the manufacture of Sitagliptin or the intermediate thereof.

In another aspect, the present application provides a method for preparing Sitagliptin or the intermediate thereof, comprising the step of using the compound of Formula I or Formula II or the pharmaceutically acceptable salt thereof, the polypeptide, or the composition as described above.

Definition and Explanation of Relevant Terms

In the present invention, unless otherwise specified, the scientific and technical terms used herein have the meanings as generally understood by a person skilled in the art. Moreover, the relevant laboratory operations used herein are the routine operations widely used in the corresponding fields. In addition, for better understanding of the present invention, the definitions and explanations of relevant terms are provided as follows.

As used herein, the term "identity" refers to the match degree between two polypeptides or two nucleic acids. When two sequences for comparison have the same base or amino acid monomer sub-unit at a certain site (e.g., each of the two DNA molecules has an adenine at a certain site, or each of the two polypeptides has a lysine at a certain site), the two sequences are identical at the site. The percentage of sequence identity is determined by comparing two optimally aligned sequences over a comparison window, wherein the portion of the polypeptides or nucleic acids sequence in the comparison window may comprise additions or deletions (i.e., gaps) as compared to the reference sequence for optimal alignment of the two sequence. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the expression "nucleic acid/polypeptide is heterogenous for a cell" means that the nucleic acid/polypeptide is not naturally occurring in the cell. That is, the cell in its natural state does not comprise or express the nucleic acid/polypeptide.

As used herein, the expression "nucleic acid/polypeptide is exogenous for a cell" means that the nucleic acid/polypeptide is exogenously introduced into the cell by human manipulation. It should be understood that, corresponding to the natural or native form of the nucleic acid/polypeptide, the exogenous nucleic acid/polypeptide has been modified in a manner that would not otherwise exist in nature, or is identical thereto but produced or derived from synthetic materials and/or by manipulation using recombinant techniques. Non-limiting examples include, among others, recombinant cells expressing genes that are not found within the native form of the cell or express native genes that are otherwise express at a different level.

As used herein, the term "$C_{1-6}$alkyl" refers to a linear or branched alkyl having 1~6, i.e. 1, 2, 3, 4, 5 or 6 carbon atoms, typically, methyl, ethyl, n-propyl, isopropyl, n-butyl, isobutyl, sec-butyl, tert-butyl, neopentyl, pentyl, hexyl, etc. Similarly, the term "$C_{1-4}$alkyl" refers to a linear or branched alkyl having 1, 2, 3, or 4 carbon atoms, including methyl, ethyl, n-propyl, isopropyl, n-butyl, etc.

As used herein, the term "3-8-membered cycloalkyl" refers to a saturated cyclic hydrocarbon group containing 3-8 ring members, which may be a monocycle or a fused polycyclic system, and may be fused to an aromatic ring. It includes, for example, 3-6-membered cycloalkyl, 4-6-membered cycloalkyl, 5-6-membered cycloalkyl, etc. Non-limiting examples include cyclopropyl, cyclobutyl, cyclopentyl and cyclohexyl.

As used herein, the term "3-8-membered heterocyclic alkyl" refers to a saturated or partially saturated, monocyclic or bicyclic group containing 3-8 ring members, at least one and at most four of which are heteroatoms independently selected from the group consisting of N, O and S, for example, 3-6-membered heterocyclic alkyl, 4-6-membered heterocyclic alkyl or 5-6-membered heterocyclic alkyl. Preferably, the heteroatoms are one N atom, two N atoms, one N atom and one O atom, or one N atom and one S atom. Examples of these groups include, but are not limited to pyrrolidine ring, oxazolidine ring, isoxazolidine ring, imidazolidine ring, piperidine ring, morpholine ring, thiomorpholine ring or piperazine ring, etc.

As used herein, the term "6-10-membered aryl" refers to an aromatic group containing at least one aromatic ring and 6-10 ring members, e.g. phenyl, naphthyl, etc.

As used herein, the term "5-10-membered heteroaryl" refers to an aromatic group containing 5-10 ring members, at least one of which is heteroatom independently selected from the group consisting of N, O and S, e.g. 5-6-membered heteroaryl etc. Examples of these groups include, but are not limited to pyrrolyl, furyl, thienyl, imidazolyl, pyrazolyl, triazolyl, tetrazolyl, oxazolyl, isoxazolyl, oxadiazolyl, thiazolyl, isothiazolyl, thiadiazolyl, pyridyl, pyrimidyl, triazinyl, benzimidazolyl, benzoxazolyl, benzothiazolyl, benzofuranyl, benzothienyl, indolyl, isoindolyl, pyridazinyl, pyrazinyl, quinolinyl, etc.

As used herein, the term "4-7-membered heterocycle" refers to a cyclic group containing 4-7 ring members, at least one of which is heteroatom independently selected form the group consisting of N, O and S. It includes 4-7-membered aliphatic heterocycle and aromatic heterocycle, e.g. 5-6-membered aliphatic heterocycle, 5-6-membered aromatic heterocycle. Particular examples include, but are not limited to pyrrolidine ring, imidazolidine ring, oxazolidine ring, isoxazolidine ring, piperidine ring, piperazine ring, morpholine ring, thiomorpholine ring, pyrrole ring, imidazole ring, oxazole ring, imidazole ring, pyrazole ring, triazole ring, tetrazole ring, oxazole ring, isoxazole ring, oxadiazole ring, thiazole ring, isothiazole ring, thiadiazole ring, pyridine ring, pyrimidine ring, triazine ring, pyridazine ring, pyrazine ring, etc.

The amino acids and abbreviations used herein have the following corresponding relationships:

| Name | Three-letter | One-letter |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Beneficial Effects of the Invention

The present application provides a polypeptide or a composition comprising the polypeptide, which can stereospecifically catalyze β-carbonyl amide to produce (R)-chiral amine, and therefore is used in the synthesis of Sitagliptin. As compared with the prior art, the method for the synthesis of Sitagliptin and construction of its chiral center provided in the present application have advantages, such as low cost, easy to operate, low environmental pollution, higher total yield and/or high purity and enantiomeric excess of product, and therefore are suitable for industrial production.

The embodiments of the invention are illustrated in detail by reference to the following drawings and examples. However, it is understood by those skilled in the art that the following drawings and examples are used only for the purpose of illustrating the invention, rather than limiting the protection scope of the invention. According to the detailed description of the following drawings and preferred embodiments, various purposes and advantages of the invention are obvious for those skilled in the art. When the conditions are not indicated in the Examples, the Examples are carried out under the conventional conditions or the conditions recommended by the manufacturers. The reagents or instruments, the manufacturers of which are not indicated, are the conventional products that are commercially available.

SEQUENCE INFORMATION

Figure 1:
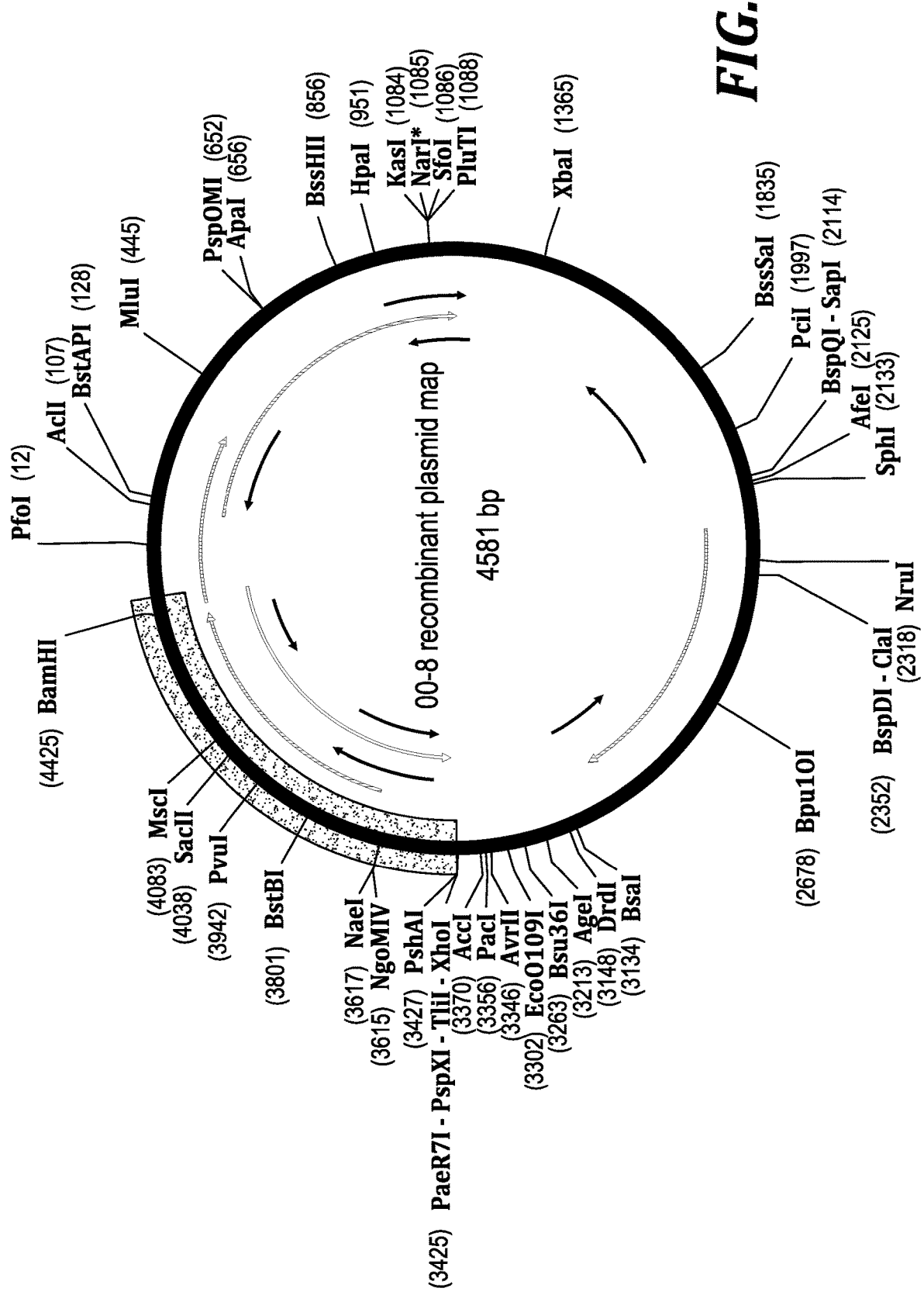
FIG. 1 shows the 00-8 recombinant plasmid map.

Information of the sequences involved in the present invention is provided in the following Table 1.

TABLE 1

| SEQ ID NO: | Description of sequences |
|---|---|
| 1 | the amino acid sequence of Arthrobacter-derived transaminase mutant 1 |
| 2 | the gene sequence of Arthrobacter-derived transaminase mutant 1 |
| 3 | the amino acid sequence of Arthrobacter-derived transaminase mutant 2 |
| 4 | the gene sequence of Arthrobacter-derived transaminase mutant 2 |
| 5 | the amino acid sequence of Arthrobacter-derived transaminase mutant 3 |
| 6 | the gene sequence of Arthrobacter-derived transaminase mutant 3 |
| 7 | the amino acid sequence of Arthrobacter-derived transaminase mutant 4 |
| 8 | the gene sequence of Arthrobacter-derived transaminase mutant 4 |

Sequence 1

(SEQ ID NO: 1)

SVLHRGQQRRRFHIQFPVTTDNALGNRTRHTVRNGITIDRNERPDATAGGATQNFVSIVQFCRRDIGQNRFVAQRFRDFQNG

LARNTRQSCTTRATNHTIFDDNHIKARTFSQQVVTIQQQRQFETAIMGFLDCTNQVAPLKVLHLRINGTTRGATDALCNHQV

HTVADTIERNNPLVRARTHIHLRAMFGDITFKRRRAIAAGNRHGDHGFTQFGLGHQFQRDFFDFILRQRRDQANRFCIAEQAF

NVVAQTESITVPNMKRGVGCVRRIETLIKDGNTGFTRRHKRTLNPCCTASQRVCRVQFVVAVGNVVQARIVGVNNFRRVCG

ECHRILAVVMMVMAA

Sequence 2

(SEQ ID NO: 2)

ATGGCCTCTATGGACAAAGTCTTTTCGGGATATTATGCGCGCCAGAAGCTGCTTGAACGGAGCGACAATCCTTTCTCTAAG

GGCATTGCTTATGTGGAAGGAAAGCTCGTCTTTCCTAGTGATGCTAGAATACCGCTACTCGACGAAGGTTTCATGCACAGT

GACCTAACCTATGATGTTATATCGGTTTGGGATGGTCGCTTCTTTCGATTGGACGATCATTTGCAACGGATTTTGGAAAGC

TGCGATAAGATGCGGCTCAAGTTCCCACTTGCACTGAGCACCGTGGAAAATATTCTGGCTGAGATGGTCGCCAAGAGTGG

TATCCGGGATGCGTTTGTGGAAGTTATTGTGACACGTGGTCTGACAGGTGTACGTGGTTCGAAGCCTGAGGATCTGTATA

ATAACAACATATACCTGCTTGTTCTTCCATACATTTGGGTTATGGCGCCTGAGAACCAGCTCCATGGTGGCGAGGCTATCA

TTACAAGGACAGTGCGACGAACACCCCCAGGTGCATTTGATCCTACTATCAAAAATCTACAGTGGGGTGATTTAACAAAG

GGACTTTTTGAGGCAATGGACCGTGGCGCCACATACCCATTTCTCACTGATGGAGACACCAACCTTACTGAAGGATCTGGT

TTCAACATTGTTTTGGTGAAGAACGGTATTATCTATACCCCTGATCGAGGTGTCTTGCGAGGGATCACACGTAAAAGTGTG

ATTGACGTTGCCCGAGCCAACAGCATCGACATCCGCCTTGAGGTCGTACCAGTGGAGCAGGCTTATCACTCTGATGAGAT

CTTCATGTGCACAACTGCCGGCGGCATTATGCCTATAACATTGCTTGATGGTCAACCTGTTAATGACGGCCAGGTTGGCCC

AATCACAAAGAAGATATGGGATGGCTATTGGGAGATGCACTACAATCCGGCGTATAGTTTTCCTGTTGACTATGGCAGTG

GCTAA

-continued

Sequence 3

(SEQ ID NO: 3)

AAAITIITTARIRYCTGVSREEDSTFSSQGRRMIDWVTGPGTPSEIGLPSTETNGQTPPPVVQPRTSSASSSSARVMSARIASGP

RDSAISRTVLRVIPGRAAASRPSPSSSSGASKPRSWVSGTARIRSPHWKFLTCGSIEERGVRRTDGATIAGTPSRMRSNGTIHW

YGTAYMGTCGRCLVMSRSPGVEEGPRVIETETTASRSSVLATSSRAISLTSSWVSGGMIRIDSALENRRSMWSSRRKALPFQT

WNPVGVTSECRGPWSKIEIRASDGGTKAPSIQAAPPASGLAGSSSGSEGVIGSRPVSWVGTISEVSAEKA

Sequence 4

(SEQ ID NO: 4)

GCAGCAGCCATCACCATCATCACCACAGCCAGGATCCGGTACTGTACCGGGGTCAGCAGAGAAGAAGATTCAACGTTCAG

TTCCCAGTAACGACGGATGATAGACTGGGTAACCGGACCCGGAACACCGTCAGAGATCGGGTTACCGTCAACAGAAACG

AACGGCCAAACACCACCACCGGTAGTGCAACCCAGAACTTCGTCAGCGTCCAGCAGTTCAGCCAGGGTGATGTCAGCCAG

GATAGCTTCGTGACCCAGAGATTCAGCGATTTCCAGAACGGTTTTACGGGTGATACCCGGCAGAGCAGCAGCCAGCAGAC

CGTCACCGTCCAGCAGCAGCGGAGCTTCGAAACCACGGTCGTGGGTTTCCTGAACTGCACGGATCAGGTCACCCCACTGG

AAGTTTTTAACCTGCGGGTCGATAGAAGAACGCGGAGTACGACGAACAGACTGAGCAACCATAGCGTGAACACCGTCAC

GGATGCGGTCAAACGGTACGATCCACTGGTACGGAACAGCGTACATGTAAACCTGCGGACGATGTTTGGTGATGTCACGT

TCACCTGGGGTAGAAGAGTAACCACGGGTGATAGAAACAGAAACGACTGCTTCACGCAGTTCGGTTTTAGCAACCAGTTC

CAGAGCGATTTCTTTAACTTCGTCCTGGGTCAGCGGCGGATGATACGCATAGATTCAGCGTTAGAGAACAGACGTTCGA

TGTGGTCGTCCAGACGGAAAGCGTTACCGTTCCAAACGTGGAACCCGGTGTAGGTAACGTCAGAGTGCAGGTAACCCTG

GTCGAAGATAGAGATACGAGCTTCAGACGGCGGAACGAAAGCACCTTCGATCCAAGCAGCACCACCAGCCAGCGGGTTA

GCCGGGTCCAGTTCGTAGTCAGAGTAGGTGATATAGTCCAGACCGGTGTCGTGGGTGTAAACGATTTCAGAGGTGTCAG

CAGAGAAAGCCAT

Sequence 5

(SEQ ID NO: 5)

AAAITIITTARIRYCTGVSREEDSTFSSQGRRMIDWVTGPGTPSEIGLPSTETNGQTPPPVEQPRTSSASSSSARVMSARIASGP

RDSAISRTVLRVIPGRAARPGERTTPSLITTTLKPGPSASRPSPSSSSGSSKPRSWVSGIARIRSPHWKFLTCGSIEERGVRRTDGA

TIAGTPSRMRSNGTIHWYGTAYMGTCGRCLVMSRIYGVEEGPRVIETETIASRSSVLATSSRAISLTSSWVSGGMIRIDSALENR

RSMWSSRRKALPFQTWNPVGVASEVRGPWSKIEIRASDGGTKAPSIQAAPPASGLAGSSSWSEGVIGSRPVSWVGTISEVSA

EKA

Sequence 6

(SEQ ID NO: 6)

GCAGCAGCCATCACCATCATCACCACAGCCAGGATCCGGTACTGTACCGGGGTCAGCAGAGAAGAAGATTCAACGTTCAG

TTCCCAGTAACGACGGATGATAGACTGGGTAACCGGACCCGGAACACCGTCAGAGATCGGGTTACCGTCAACAGAAACG

AACGGCCAAACACCACCACCGGTTGAGCAACCCAGAACTTCGTCAGCGTCCAGCAGTTCAGCCAGGGTGATGTCAGCCAG

GATAGCTTCGTGACCCAGAGATTCAGCGATTTCCAGAACGGTTTTACGGGTGATACCCGGCAGAGCAGCACGACCCGGAG

AACGAACAACACCGTCTTTGATAACAACAACGTTGAAACCCGGACCTTCAGCCAGCAGACCGTCACCGTCCAGCAGCAGC

GGCAGCTCGAAACCACGGTCGTGGGTTTCCTGAATTGCACGGATCAGGTCACCCCACTGGAAGTTTTTAACCTGCGGGTC

GATAGAAGAACGCGGAGTACGACGAACAGACTGAGCAACCATAGCGTGAACACCGTCACGGATGCGGTCAAACGGTAC

GATCCACTGGTACGGAACAGCGTACATGTAAACCTGCGGACGATGTTTGGTGATGTCACGAATATATGGGGTAGAAGAG

TAACCACGGGTGATAGAAACAGAAACGATTGCTTCACGCAGTTCGGTTTTAGCAACCAGTTCCAGAGCGATTTCTTTAACT

TCGTCCTGGGTCAGCGGCGGATGATACGCATAGATTCAGCGTTAGAGAACAGACGTTCGATGTGGTCGTCCAGACGGA

AAGCGTTACCGTTCCAAACGTGGAACCCGGTGTAGGTAGCGTCAGAGGTCAGGTAACCCTGGTCGAAGATAGAGATACG

AGCTTCAGACGGCGGAACGAAAGCACCTTCGATCCAAGCAGCACCACCAGCCAGCGGGTTAGCCGGGTCCAGTTCGTGG

TCAGAGTAGGTGATATAGTCCAGACCGGTGTCGTGGGTGTAAACGATTTCAGAGGTGTCAGCAGAGAAAGCCAT

```
Sequence 7
                                                                         (SEQ ID NO: 7)
AAAITIITTARIRYCTGVSREEDSTFSSQGRRMIDWVTGPGTPSEIGLPSTETNGQTPPPVEQPRTSSASSSSARVMSARIASGP RDSAISRTVLRVIPGRAARPGERTTPSLITTTLKPGPSASRPSQSSSSGSSKPRSWVSGIARIRSPHWKFLTCGSIEERGVRRTDG ATIAGTPSRMRSNGTIHWYGTAYMGTCGRCLVMSRSNGVEEGPRVIETETIASRSSVLATSSRAISLTSSWVSGGMIRIDSALE NRRSMWSSRRKALPFQTWKVVGVASEVGGPWSKIEIRASDGGTKAPSIQAAPPASGLAGSSSGSEGVIGSRPVSWVGTISEV

SAEKA

Sequence 8
                                                                         (SEQ ID NO: 8)
GCAGCAGCCATCACCATCATCACCACAGCCAGGATCCGGTACTGTACCGGGGTCAGCAGAGAAGAAGATTCAACGTTCAG

TTCCCAGTAACGACGGATGATAGACTGGGTAACCGGACCCGGAACACCGTCAGAGATCGGGTTACCGTCAACAGAAACG

AACGGCCAAACACCACCACCGGTTGAGCAACCCAGAACTTCGTCAGCGTCCAGCAGTTCAGCCAGGGTGATGTCAGCCAG

GATAGCTTCGTGACCCAGAGATTCAGCGATTTCCAGAACGGTTTTACGGGTGATACCCGGCAGAGCAGCACGACCCGGAG

AACGAACAACACCGTCTTTGATAACAACAACGTTGAAACCCGGACCTTCAGCCAGCAGACCGTCGCAGTCCAGCAGCAGC

GGCAGCTCGAAACCACGGTCGTGGGTTTCCTGAATTGCACGGATCAGGTCACCCCACTGGAAGTTTTTAACCTGCGGGTC

GATAGAAGAACGCGGAGTACGACGAACAGACTGAGCAACCATAGCGTGAACACCGTCACGGATGCGGTCAAACGGTAC

GATCCACTGGTACGGAACAGCGTACATGTAAACCTGCGGACGATGTTTGGTGATGTCACGCTCGAATGGGGTAGAAGAG

TAACCACGGGTGATAGAAACAGAAACGATTGCTTCACGCAGTTCGGTTTTAGCAACCAGTTCCAGAGCGATCTCTTTAACT

TCGTCCTGGGTCAGCGGCGGGATGATACGGATAGATTCCGCGTTAGAGAACAGACGTTCGATGTGGTCGTCCAGACGGA

AAGCGTTACCGTTCCAAACGTGGAAGGTGGTGTAGGTAGCGTCAGAAGTATAGTAACCCTGGTCGAAGATAGAGATACG

AGCTTCAGACGGCGGAACGAAAGCACCTTCGATCCAAGCAGCACCACCAGCCAGCGGGTTAGCCGGGTCCAGTTCGTAGT

CAGAGTAGGTGATATAGTCCAGACCGGTGTCGTGGGTGTAAACGATTTCAGAGGTGTCAGCTGAGAAAGCCAT
```

SPECIFIC MODES FOR CARRYING OUT THE INVENTION

The invention is illustrated by reference to the following examples which are intended to exemplify the present invention, rather than limiting the protection scope of the present invention.

Unless indicated otherwise, the molecular biological experimental methods used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, $3^{rd}$ Edition, John Wiley & Sons, Inc., 1995. The assays used here are the conventional assays in the art, and are carried out according to the steps described in the relevant documents or according to the steps recommended by the manufacturers of the instruments used.

Example 1 Expression of Mutant Proteins of Transaminase from *Arthrobacter*

Figure 2:
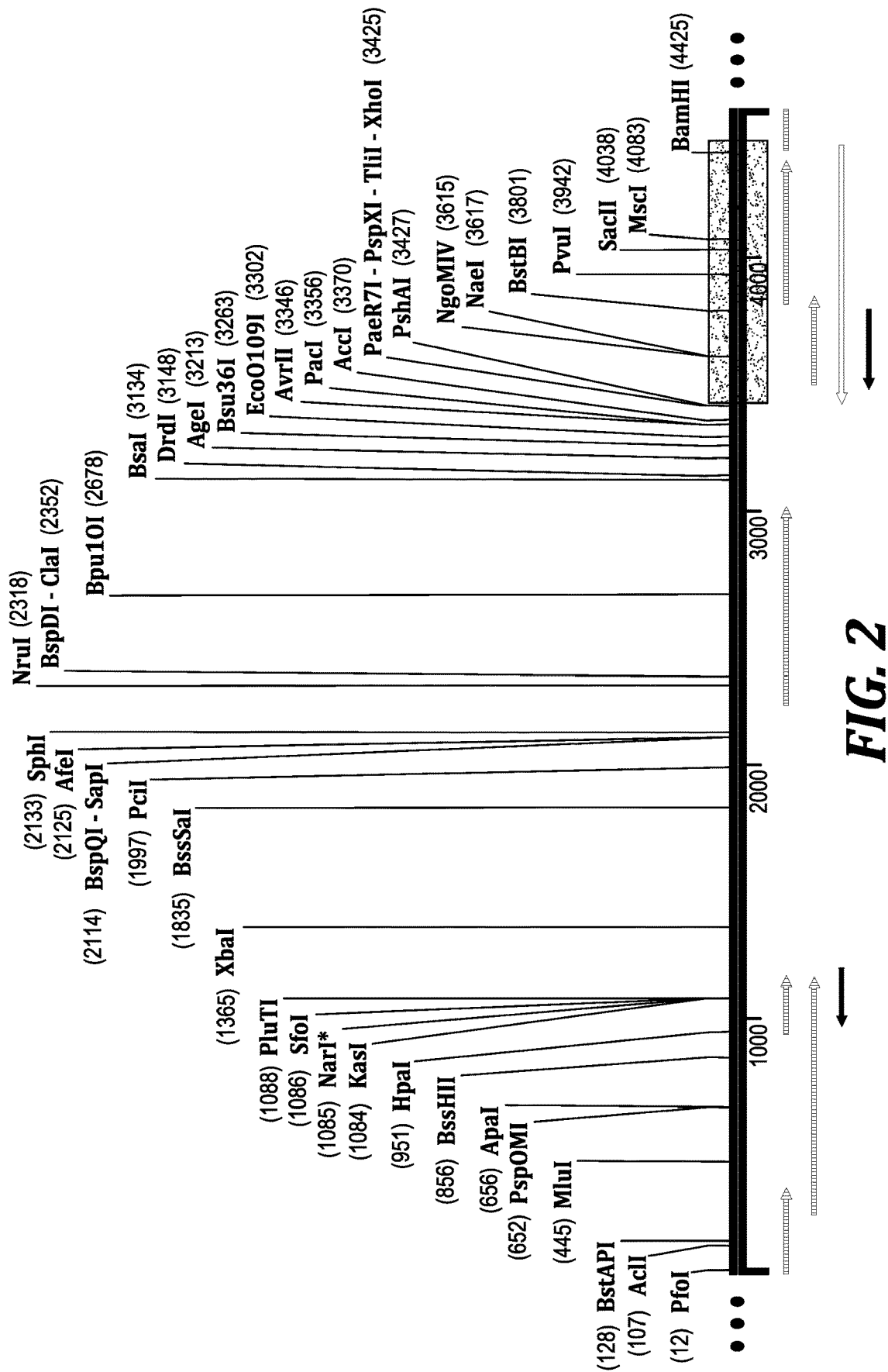
FIG. 2 shows the enzyme cleavage sites for 00-8 recombinant plasmid.

The wild-type gene sequence of transaminase from *Arthrobacter* was designed artificially, and the designed gene sequences were set forth in SEQ ID 2, 4, 6 and 8. These sequences were obtained by total gene synthesis, and were cloned into plasmid PET24a at two restriction enzyme recognition sites XhoI and NcoI. The plasmid constructed above was transfected into *E. coli* DH5α competent cells. The positive transformants were selected and identified by sequencing to afford the recombinant expression vector, which was named as 00-8 plasmid (see FIG. 1 and FIG. 2).

The recombinant expression vector, 00-8 plasmid, was transfected into *E. coli* BL21 (DE3) strain, thereby obtaining the genetically engineered bacteria that could induce the expression of mutants of transaminase from *Arthrobacter*.

The genetically engineered bacteria obtained above were subjected to streak culture on kanamycin-resistant LB solid medium in a 37° C. biochemical incubator overnight. Large colonies were seeded in kanamycin-resistant LB liquid medium, and incubated in a shaker at 37° C., 220 rpm for 6~8 h, or incubated at 30° C., 200 rpm overnight, thereby obtaining a primary seed culture. The primary seed culture was seeded into kanamycin-resistant TB liquid medium at a seeding amount of 1%, and incubated in a shaker at 37° C., 220 rpm for 4~6 h. When the bacterial solution was observed to be turbid, a secondary seed culture was obtained. The secondary seed culture was seeded to a fermenter at a seeding amount of 1% (the secondary seed culture was seeded into three fermenters, respectively, and the formulations of the media contained in the fermenters were shown in Table 2). Initial control: incubated at 37° C. under a constant pressure with air introduced. When the dissolved oxygen level reduced, it was enhanced by gradually increasing ventilatory capacity, rotational speed, and the pressure of fermenter, wherein the pressure of fermenter was not higher than 0.08 MPa. During fermentation, a supplementary medium was added (the formulation of the supplementary medium was shown in Table 3), so as to control the dissolved oxygen level between 20-40%. When OD600 reached about 25, the temperature was reduced to 28° C., 30° C. and 25° C., respectively, and IPTG was added at a concentration of 0.15 mM, 0.2 mM and 0.3 mM, respectively. The fermentation broth was subjected to centrifugation or membrane filtration to collect bacteria, and the collected bacteria were washed with a phosphate buffer, and then subjected to cell disruption in an ultrasonic disrupter or a high pressure homogenizer. The cell disrupting solution was subjected to centrifugation or membrane filtration, thereby obtaining a crude Mutant 1, which was dissolved in a pH 8.0 $KH_2PO_4$ buffer at a mass concentration of 10-20% for further use.

TABLE 2

Formulations of media in fermenters (exemplified as a 30 L fermentation liquid, unit: g)

| No. | Ingredient | Group I | Group II | Group III |
|---|---|---|---|---|
| 1 | dipotassium hydrogen phosphate | 194 | 294 | 294 |
| 2 | potassium dihydrogen phosphate | 30 | 33 | 30 |
| 3 | ammonium sulfate | 25 | 25 | 25 |
| 4 | anhydrous magnesium sulfate | 17.2 | 17.2 | 17.2 |
| 5 | citric acid | 160 | 160 | 160 |
| 6 | glycerol | 50 | 50 | 150 |
| 7 | fish peptone | 140 | 440 | 540 |
| 8 | yeast extract powder | 360 | 160 | 360 |
| 9 | sodium chloride | 15 | 15 | 15 |
| 10 | manganese chloride tetrahydrate | 0.6 | 2 | 1.6 |
| 11 | ferric chloride | 0.6 | 0.6 | 1.6 |
| 12 | defoamer | 15 | 15 | 15 |

Note:
the ingredients were weighed and added to the fermenter, water was balanced to a suitable volume, the mixture was stirred for better disolution, and then caustic soda flake was used to adjust pH to 7.

TABLE 3

Formulation of the supplementary medium (exemplified as a 6 L supplementary medium for a 30 L fermentation liquid, unit: g)

| No. | Ingredient | Group I | Group II | Group III |
|---|---|---|---|---|
| 1 | glycerol | 7400 | 2400 | 3400 |
| 2 | fish peptone | 140 | 140 | 240 |
| 3 | yeast extract powder | 1080 | 1080 | 180 |
| 4 | magnesium sulfate | 15.6 | 14.6 | 25.6 |
| 5 | defoamer | 3 | 3 | 3 |

According to the method above, the Mutants 2-4 were obtained.

Example 2 Assay on Enzyme Activity of the Mutants

Method for Determining Enzyme Activity:

(1) Preparation of 4M isopropyl amine hydrochloride (100 mL): 100% isopropyl amine (23.64 g) was weighed and added with about 40 mL water, followed by a slow addition of HCl (about 30 mL, fuming) at a low temperature in a fume cupboard until pH reached 8.5, then volumed to 100 mL with water for further use.

(2) Preparation of an isopropyl amine aqueous solution (40% by mass).

(3) Preparation of a substrate solution: the substrate solution was prepared by dissolving the substrate 3-oxo-4-(2,4,5-trifluorophenyl)butyrylpiperazine in ethanol, at a ratio of per 100 g substrate dissolved with 200 mL ethanol, and contained in a feeding bottle at 45° C. for further use.

(4) Water (600 mL) (the total volume of water and the mutant solution prepared in example 1 was 1000 mL), 4M isopropyl amine hydrochloride (1.2 eq, 99.4 mL), TEA (3 g) and coenzyme pyridoxal phosphate (0.7 g) were added, and heated to 45° C. 40% isopropyl amine was used to adjust pH to 8.5. The mutant solution (400 mL) was added, and a suitable amount of air was introduced (whilst controlling bubbling). The substrate solution (about 270 mL in total) was fed to a reaction system at a relatively fixed rate in 5 h-7 h. The reaction was carried out at 45° C. for 12 h. During the reaction, pH was controlled at 8.5 by using 40% isopropyl amine. If the liquid level reduced, a suitable amount of pure water was added. The product was extracted with ethyl acetate, and the ethyl acetate phase was collected and concentrated. The concentrated residue was qualitatively and quantitatively determined by HPLC. The substrate conversion rate was recorded as enzyme activity index, which was used to evaluate the catalytic activity of the Mutants 1-4. The result was shown in the following table.

Comparative table of enzyme activity

| No. | SEQ ID NO. | Enzyme activity index |
|---|---|---|
| 1 | 1 | 100 |
| 2 | 3 | 30 |
| 3 | 5 | 35 |
| 4 | 7 | 40 |

Example 3 Synthesis of Sitagliptin

In the present application, 2,4,5-trifluorophenylacetic acid, Meldrum's acid, $NHR_1R_2$ and 3-trifluoromethyl-5,6,7,8-tetrahydro-[1,2,4]triazolo[4,3-a]pyrazine hydrochloride were used as raw materials; a transamination substrate β-carbonyl amide Compound I was prepared, and then the mutant of transaminase from *Arthrobacter* obtained in the present application was used to catalyze the carbonyl-to-amino conversion, thereby obtaining β-amino amide Compound II in a high optical purity; the Compound II was then subjected to hydrolysis, amino group protection, condensation with 3-trifluoromethyl-5,6,7,8-tetrahydro-[1,2,4]triazolo[4,3-a]pyrazine hydrochloride, and de-protection, thereby affording Sitagliptin in a high yield. The particular synthetic scheme was as followed:

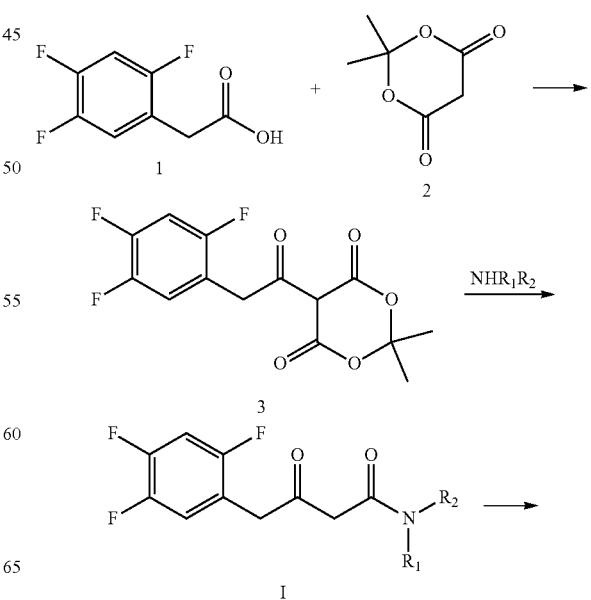

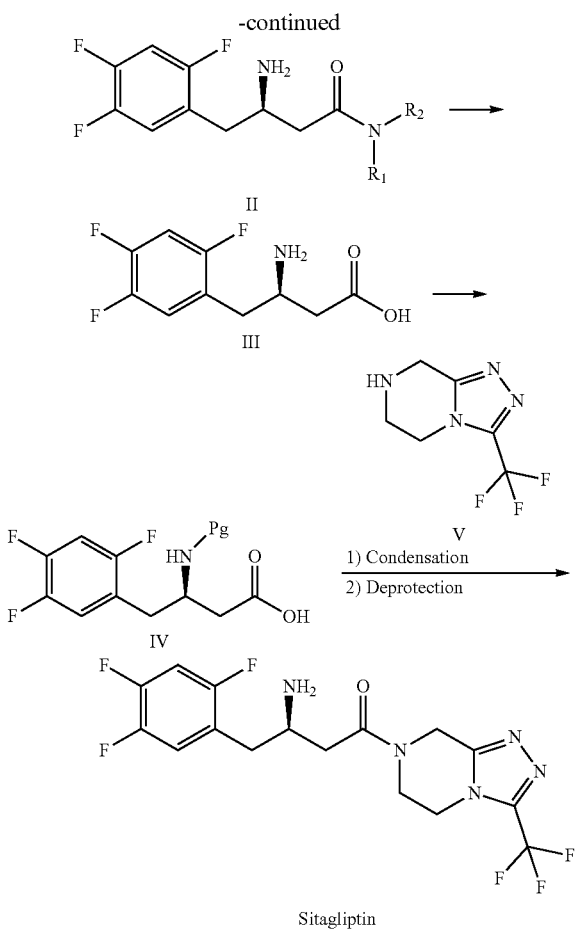

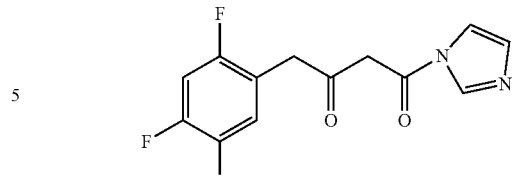

To toluene (300 ml), Compound 3 (30 g) was added, followed by the addition of imidazole (12 g) and sodium hydroxide (0.3 g). The resultant mixture was heated to 105° C. and reacted for 10 min. The resultant solution was cooled to room temperature and crystallized to obtain a crude product as a solid. The solid was washed with water and dried, providing 3-oxo-4-(2,4,5-trifluorophenyl)butyrylimidazole (25.3 g), with a purity of 99.5%, and a yield of 94%.

$^1$H NMR ($d_6$-DMSO) δ(ppm) 8.26 (1H), 7.69 (1H), 7.25 (1H), 6.73 (1H), 6.54 (1H), 3.71 (2H), 3.56 (2H).

Condition 2, wherein in Compound I, $R_1$ and $R_2$ formed a piperazine ring, and the compound of Formula I here had a structure as shown below:

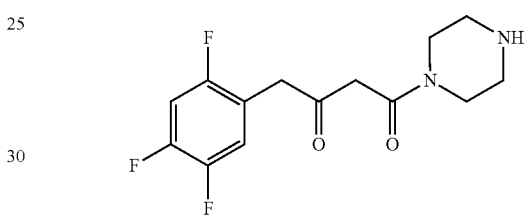

To tetrahydronaphthalene (400 ml), Compound 3 (35 g) was added, followed by the addition of piperazine (17 g). The resultant mixture was heated to 100° C., and sodium hydroxide (0.25 g) was added. After being reacted for 20 min, the resultant mixture was cooled to room temperature to obtain a crude product as a solid. The solid was washed with water and dried, providing 3-oxo-4-(2,4,5-trifluorophenyl)butyrylpiperazine (31.7 g), with a purity of 99.4%, and a yield of 95%.

$^1$H NMR ($d_6$-DMSO) δ(ppm) 6.73 (1H), 6.54 (1H), 3.71 (2H), 3.34 (2H), 3.32 (4H), 2.81 (4H), 2.0 (1H).

Condition 3, wherein in Compound I, $R_1$ and $R_2$ formed an isoxazolidine ring, and the compound of Formula I here had a structure as shown below:

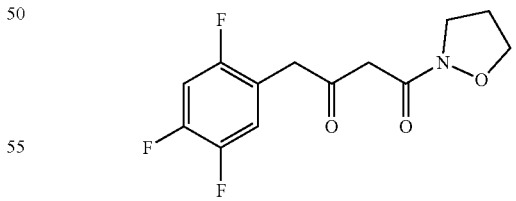

To toluene (500 ml), Compound 3 (32 g) was added, followed by the addition of 4-hydroisoxazolehydrochloride (25 g). The resultant mixture was heated to 101° C., and sodium hydroxide (40 g) was added. After being reacted for 30 min, the resultant mixture was cooled to room temperature, and filtrated. The solid was washed with water and 3-oxo-4-(2,4,5-trifluorophenyl)butyryl-4-hydroisoxazole (28 g) was obtained, with a purity of 99.4%, and a yield of 96%.

1. Synthesis of Compound 3:

Condition 1:

To diethylacetamide (800 ml), 2,4,5-trifluorophenylacetic acid (190 g) and Meldrum's acid (210 g) were added. The resultant mixture was heated to 35° C. followed by an addition of triethylamine (50 g) and reacted at this temperature for 5 h. The resultant solution was cooled to room temperature, and added with water (2000 ml). The resultant solution was acidified with hydrochloric acid to pH=2, crystallized for 2 h, and filtrated. The crystal was dried, providing the dry product of Compound 3 (303 g), with a purity of 99.2%, and a yield of 96%.

Condition 2;

To dimethylformamide (782 ml), 2,4,5-trifluorophenylacetic acid (220 g) and Meldrum's acid (260 g) were added. The resultant mixture was heated to 35° C. followed by an addition of triethylamine (61 g) and reacted at this temperature for 4-7 h. The resultant solution was cooled to room temperature, and added with water (2500 ml) and pivaloyl chloride (89 g). The resultant solution was crystallized for 2 h, and filtrated. The crystal was dried, providing the dry product of Compound 3 (348 g), with a purity of 99.1%, and a yield of 95%.

2. Synthesis of Compound I:

Condition 1, wherein in Compound I, $R_1$ and $R_2$ formed an imidazole ring, and the compound of Formula I here had a structure as shown below:

¹H NMR (d₆-DMSO) δ(ppm) 6.73 (1H), 6.54 (1H), 3.71 (2H), 3.53 (2H), 3.34 (2H), 3.20 (2H), 1.74 (2H).

Condition 4, wherein in Compound I, R₁ and R₂ formed an morpholine ring, and the compound of Formula I here had a structure as shown below:

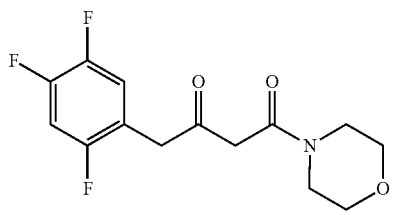 [SMILES: O=C(CC(=O)N1CCOCC1)Cc1cc(F)c(F)cc1F]

Figure 3:
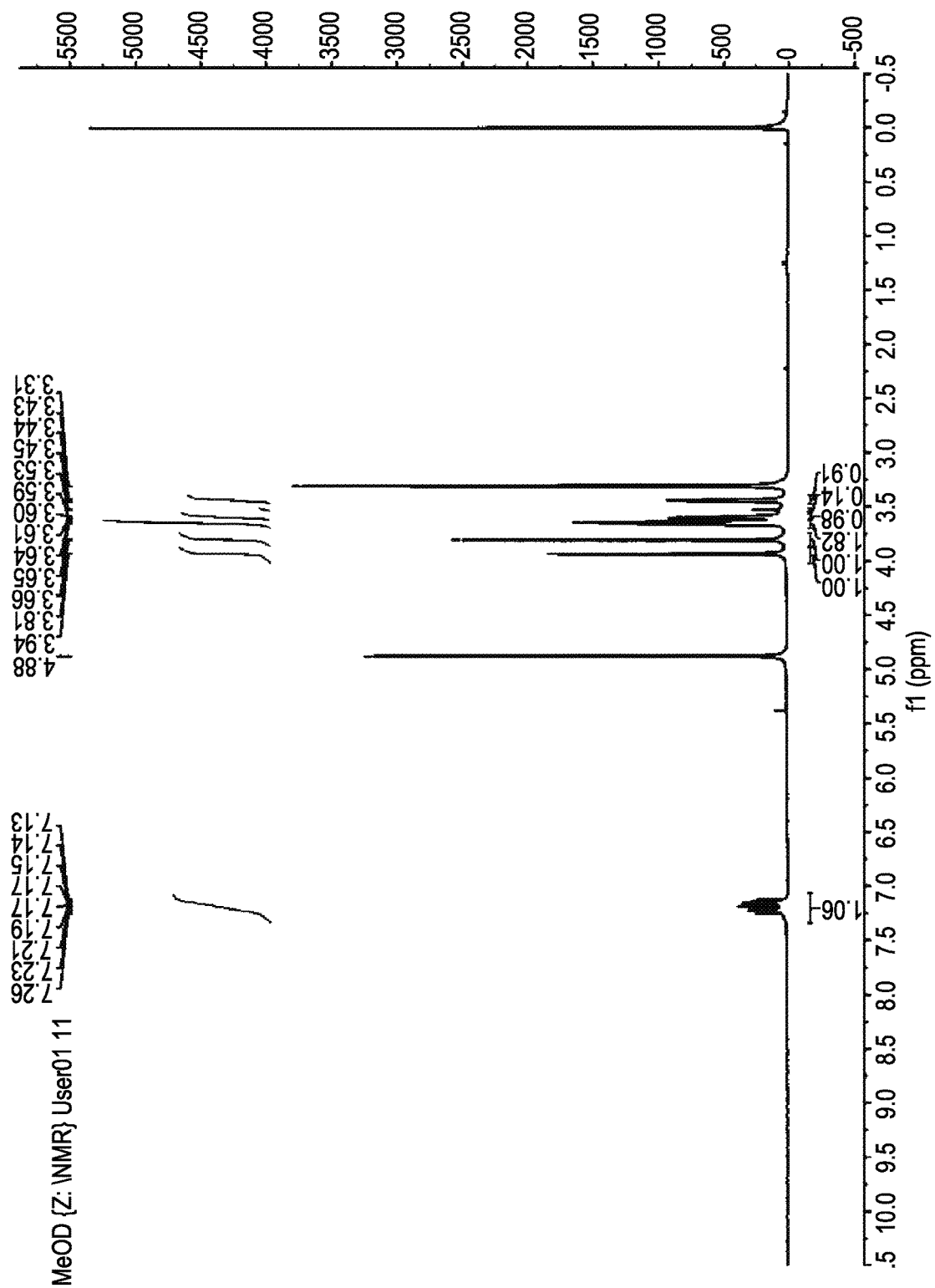
FIG. 3 shows the $^1$H NMR spectrum of Compound I prepared under Condition 4 in Example 3.2.

To toluene (90 ml) and tetralin (200 ml), Compound 3 (30 g) was added, followed by an addition of morpholine (14 g) and sodium hydroxide (0.25 g). The resultant mixture was heated to 102° C. and reacted for 30 min, then was cooled to room temperature to precipitate a crude crystal. The crystal was washed with water and 3-oxo-4-(2,4,5-trifluorophenyl)butyryl-4-morpholine (27.1 g) was obtained, with a purity of 99.4%, and a yield of 95%. ¹H NMR was shown in FIG. 3.

3. Synthesis of Compound II:
Condition 1:

4M isopropyl amine hydrochloride (100 ml), TEA (2 g), and pyridoxal phosphate (0.1 g) were added to water (1000 ml). The resultant mixture was heated to 45° C., and 40% isopropyl amine aqueous solution was used to adjust pH to 8.5. The mutant 1 solution prepared in Example 1 (600 ml) was added, and a suitable amount of air was introduced (whilst controlling bubbling). A solution of the compound 3-oxo-4-(2,4,5-trifluorophenyl)butyryl-4-hydroisoxazole (i.e. 150 g 3-oxo-4-(2,4,5-trifluorophenyl)butyryl-4-hydroisoxazole was dissolved in 40 ml methanol) was added to the reaction system at a relatively fixed flow rate in 5 h-7 h. During the addition, 40% isopropyl amine was used to control the pH. The reaction was carried out at 45° C. for 12 h, and HPLC showed a conversion rate of above 99.9%. The resultant solution was extracted with dichloromethane (200 ml), and dichloromethane was recovered and R-3-amino-4-(2,4,5-trifluorophenyl)butyryl-4-hydroisoxazole (142.5 g) was obtained, with a purity of 99.7%, and a yield of 95.0%.

¹H NMR (d₆-DMSO) δ(ppm) 6.79 (1H), 6.61 (1H), 3.32 (4H), 3.23 (1H), 2.81 (4H), 2.77 (2H), 2.40 (2H), 2.0 (1H), 2.0 (2H).

By reference to the reaction conditions above, the polypeptide with a sequence of SEQ ID NO: 86 as disclosed in the U.S. Pat. No. 8,293,507 of Codeixs Company, was used as the catalyst to catalyze the reaction above. HPLC showed a conversion rate of 22.1%.

Condition 2:

4M isopropyl amine hydrochloride (90 ml), TEA (1 g), and pyridoxal phosphate (0.5 g) were added to water (1000 ml). The resultant mixture was heated to 40° C., and 40% isopropyl amine aqueous solution was used to adjust pH to 8.0. The mutant 1 solution prepared in Example 1 (1100 ml) was added, and a suitable amount of air was introduced (whilst controlling bubbling). A solution of the compound 3-oxo-4-(2,4,5-trifluorophenyl)butyryl-piperazine (i.e. 250 g 3-oxo-4-(2,4,5-trifluorophenzyl)butyryl-piperazine was dissolved in 80 ml ethanol) was added to the reaction system at a relatively fixed flow rate in 5 h-7 h. During the addition, 40% isopropyl amine was used to control the pH. The reaction was carried out at 40° C. for 12 h, and HPLC showed a conversion rate of above 99.9%. The resultant solution was extracted with ethyl acetate (350 ml), and ethyl acetate was recovered and R-3-amino-4-(2,4,5-trifluorophenyl)butyrylpiperazine (240 g) was obtained, with a purity of 99.8%, and a yield of 96.0%.

¹H NMR (d₆-DMSO) δ(ppm) 6.79 (1H), 6.61 (1H), 3.32 (2H), 3.23 (1H), 3.34 (2H), 3.20 (2H), 1.74 (2H).

By reference to the reaction conditions above, the polypeptide with a sequence of SEQ ID NO: 86 as disclosed in the U.S. Pat. No. 8,293,507 of Codeixs Company, was used as the catalyst to catalyze the reaction above. HPLC showed a conversion rate of 12%.

Condition 3:

4M isopropyl amine hydrochloride (95 ml), TEA (1.9 g), and pyridoxal phosphate (0.2 g) were added to water (325 ml). The resultant mixture was heated to 45° C., and 40% isopropyl amine aqueous solution was used to adjust pH to 8.5. The mutant 1 solution prepared in Example 1 (625 ml) was added, and a suitable amount of air was introduced (whilst controlling bubbling). A solution of the compound 3-oxo-4-(2,4,5-trifluorophenyl)butyryl-4-morpholine (i.e. 160 g 3-oxo-4-(2,4,5-trifluorophenzyl)butyryl-4-morpholine was dissolved in 45 ml methanol) was added to the reaction system at a relatively fixed flow rate in 5 h-7 h. During the addition, 40% isopropyl amine was used to control the pH. The reaction was carried out at 45° C. for 12 h, and HPLC showed a conversion rate of above 99.9%. The resultant solution was extracted with dichloromethane (200 ml), and dichloromethane was recovered, and R-3-amino-4-(2,4,5-trifluorophenyl)butyryl-4-morpholine (154 g) was obtained, with a purity of 99.4%, and a yield of 96.3%.

¹H NMR (d₆-DMSO) δ(ppm) 6.79 (1H), 6.61 (1H), 3.67 (4H), 3.47 (4H), 3.23 (1H), 2.77 (2H), 2.40 (2H) 2.0 (2H).

Condition 4:

4M isopropyl amine hydrochloride (100 ml), TEA (2 g), and pyridoxal phosphate (0.1 g) were added to water (400 ml). The resultant mixture was heated to 45° C., and 40% isopropyl amine aqueous solution was used to adjust pH to 8.5. The mutant 1 solution (600 ml) was added, and a suitable amount of air was introduced (whilst controlling bubbling). A solution of the compound 3-oxo-4-(2,4,5-trifluorophenyl)butyryl-4-hydroisoxazole (i.e. 150 g 3-oxo-4-(2,4,5-trifluorophenyl)butyryl-4-hydroisoxazole was dissolved in 40 ml methanol) was added to the reaction system at a relatively fixed flow rate in 5 h-7 h. During the addition, 40% isopropyl amine was used to control the pH. The reaction was carried out at 45° C. for 12 h, and HPLC showed a conversion rate of above 99.9%. The resultant solution was extracted with dichloromethane (200 ml), and dichloromethane was recovered, and R-3-amino-4-(2,4,5-trifluorophenyl)butyryl-4-hydroisoxazole (144.5 g) was obtained, with a purity of 99.8%, and a yield of 96.3%.

¹H NMR (d₆-DMSO) δ(ppm) 6.79 (1H), 6.61 (1H), 3.32 (4H), 3.23 (1H), 2.81 (4H), 2.77 (2H), 2.40 (2H), 2.0 (1H), 2.0 (2H).

By reference to the reaction conditions above, the polypeptide with a sequence of SEQ ID NO: 86 as disclosed in the U.S. Pat. No. 8,293,507 of Codeixs Company, was used as the catalyst to catalyze the reaction above. HPLC showed a conversion rate of 18%.

Condition 5:

4M isopropyl amine hydrochloride (90 ml), TEA (1 g), and pyridoxal phosphate (0.5 g) were added to water (300 ml). The resultant mixture was heated to 40° C., and 40% isopropyl amine aqueous solution was used to adjust pH to 8.0. The mutant 1 solution prepared in Example 1 (750 ml)

was added, and a suitable amount of air was introduced (whilst controlling bubbling). A solution of the compound 3-oxo-4-(2,4,5-trifluorophenyl)butyryl-piperazine (i.e. 250 g 3-oxo-4-(2,4,5-trifluorophenzyl)butyryl-piperazine was dissolved in 80 ml ethanol) was added to the reaction system at a relatively fixed flow rate in 5 h-7 h. During the addition, 40% isopropyl amine was used to control the pH. The reaction was carried out at 40° C. for 12 h, and HPLC showed a conversion rate of above 99.9%. The resultant solution was extracted with ethyl acetate (350 ml), and ethyl acetate was recovered and R-3-amino-4-(2,4,5-trifluorophenyl)butyrylpiperazine (242 g) was obtained, with a purity of 99.6%, and a yield of 96.8%.

$^1$H NMR (d$_6$-DMSO) δ(ppm) 6.79 (1H), 6.61 (1H), 3.32 (2H), 3.23 (1H), 3.34 (2H), 3.20 (2H), 1.74 (2H).

By reference to the reaction conditions above, the polypeptide with a sequence of SEQ ID NO: 86 as disclosed in the U.S. Pat. No. 8,293,507 of Codeixs Company, was used as the catalyst to catalyze the reaction above. HPLC showed a conversion rate of 13%.

Figure 4:
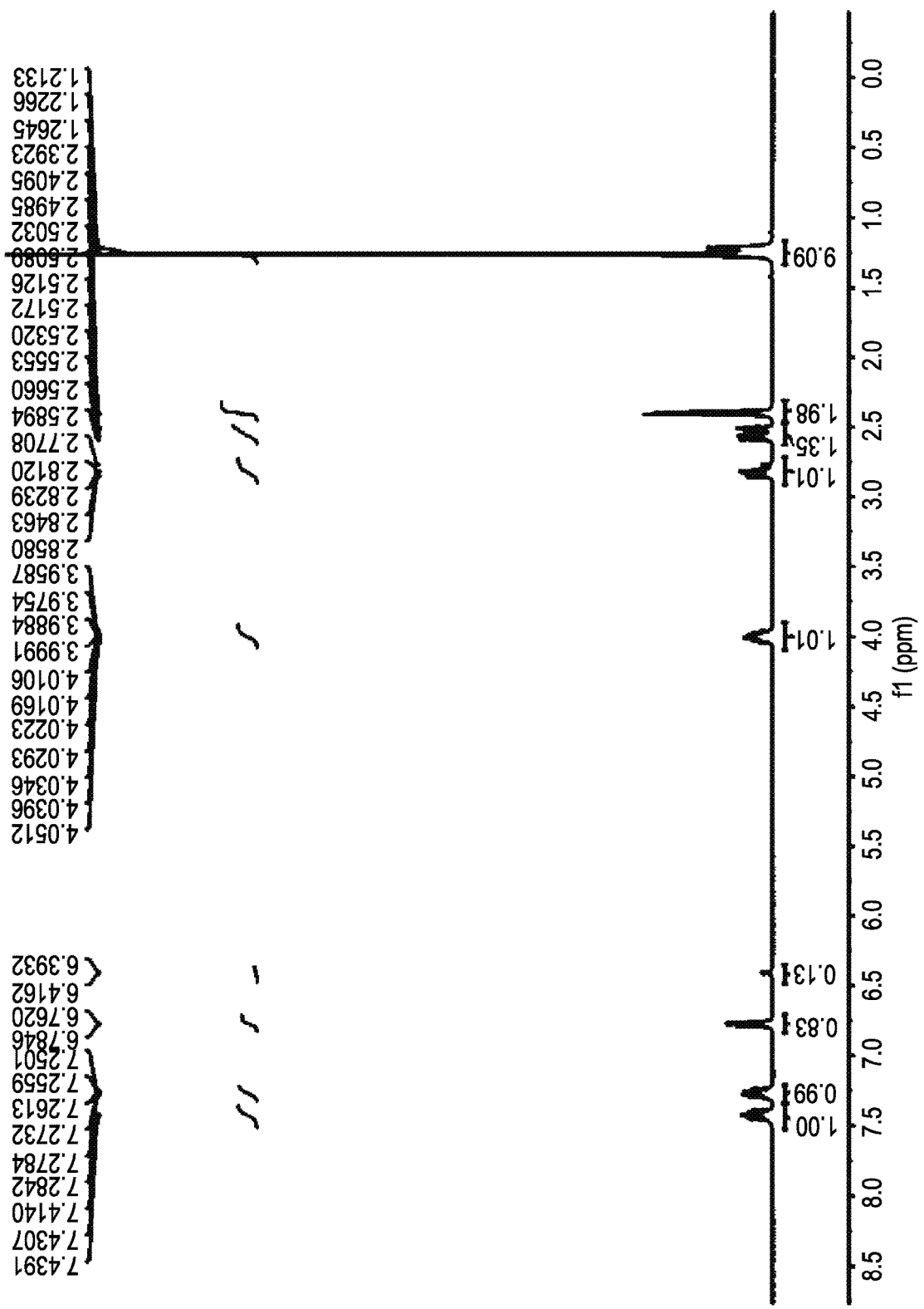
FIG. 4 shows the $^1$H NMR spectrum of Compound IV prepared under Condition 1 in Example 3.4.

4. Synthesis of Compound IV:

Condition 1:

To water (500 ml), R-3-amino-4-(2,4,5-trifluorophenyl)butyryl-4-hydroisoxazole (80 g) and sodium hydroxide (27 g) were added respectively. The resultant mixture was heated to 50° C. and reacted for 2 h. After cooling to room temperature, Boc anhydride (91 g) was added. The reaction was carried out at room temperature for 4-5 h. Then the resultant solution was acidified with hydrochloric acid to pH=1.5, crystallized and filtrated. The crystal was washed with water, and dried, affording the product (88.8 g), with a yield of 96%, and a chemical purity of 99.5%. The $^1$H NMR spectrum of the product was shown in FIG. 4.

Figure 5:
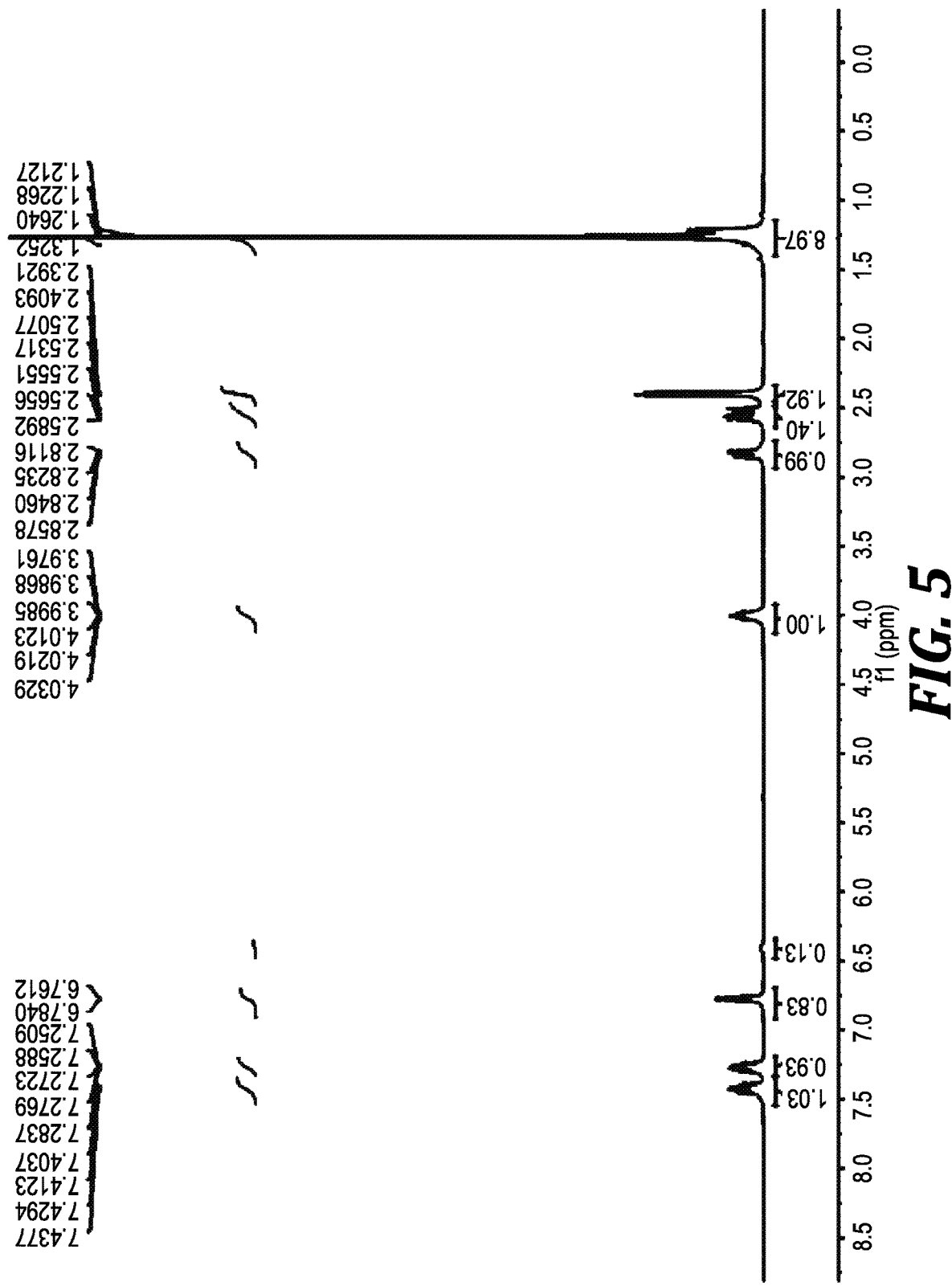
FIG. 5 shows the $^1$H NMR spectrum of Compound IV prepared under Condition 2 in Example 3.4.

Condition 2:

To water (350 ml), R-3-amino-4-(2,4,5-trifluorophenyl)butyrylpiperazine (30 g) and sodium hydroxide (10 g) were added respectively. The resultant mixture was heated to 60° C. and reacted for 3 h. After cooling to room temperature, Boc anhydride (43 g) was added. The reaction was carried out at room temperature for 6 h. Then the resultant solution was acidified with hydrochloric acid to pH=1.7, crystallized and filtrated. The crystal was washed with water, and dried, affording the product (31.5 g), with a yield of 95%, and a chemical purity of 99.4%. The $^1$H NMR spectrum of the product was shown in FIG. 5.

Figure 6:
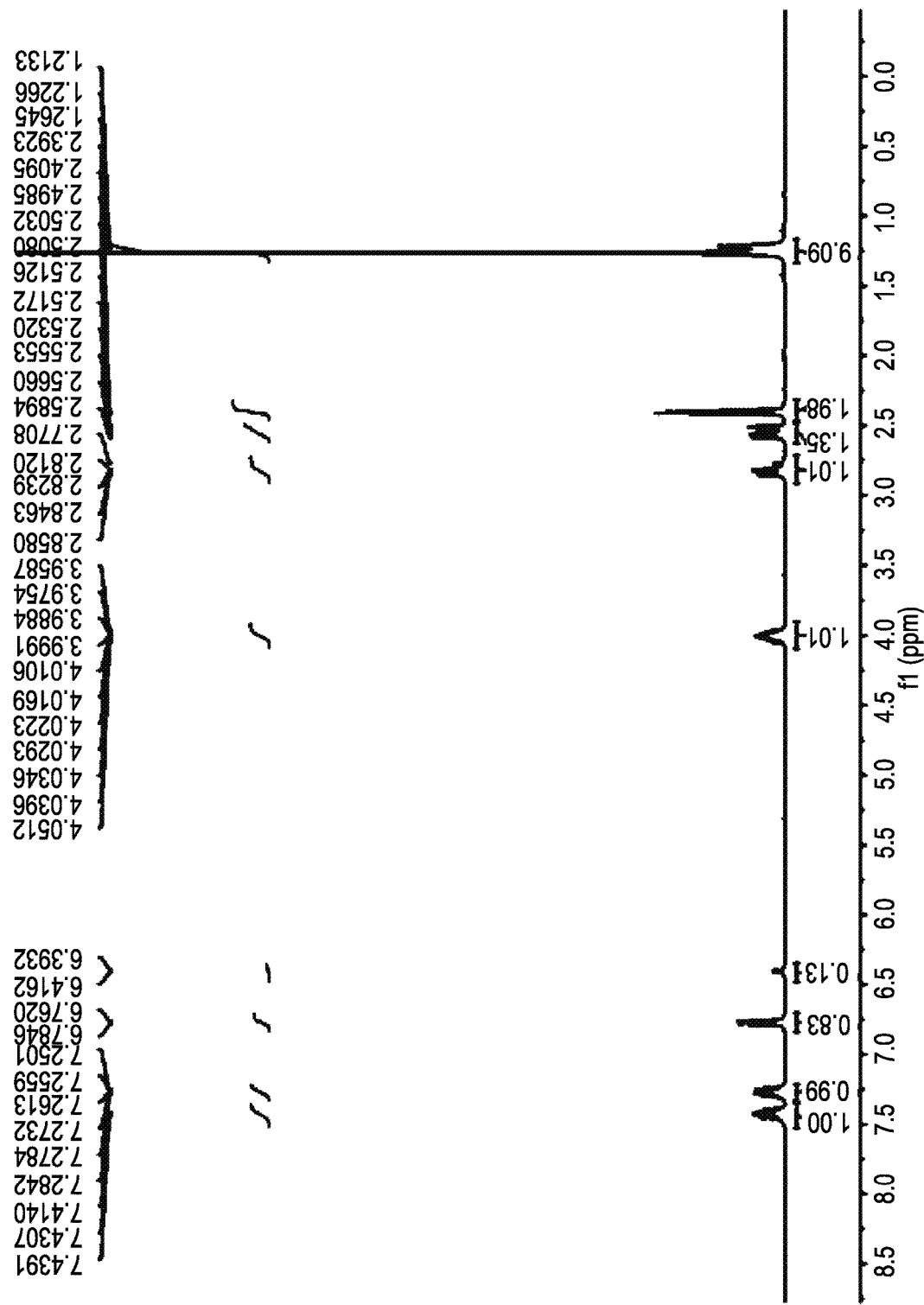
FIG. 6 shows the $^1$H NMR spectrum of Compound IV prepared under Condition 3 in Example 3.4.

Condition 3:

To water (350 ml), R-3-amino-4-(2,4,5-trifluorophenyl)butyryl-4-morpholine (30 g) and sodium hydroxide (8 g) were added respectively. The resultant mixture was heated to 58° C. and reacted for 2.5 h. After cooling to room temperature, Boc anhydride (46 g) was added. The reaction was carried out at room temperature for 5 h. Then the resultant solution was acidified with hydrochloric acid to pH=1.7, crystallized and filtrated. The crystal was washed with water, and dried, affording the product (31.8 g), with a yield of 96%, and a chemical purity of 99.5%. The $^1$H NMR spectrum of the product was shown in FIG. 6.

Figure 7:
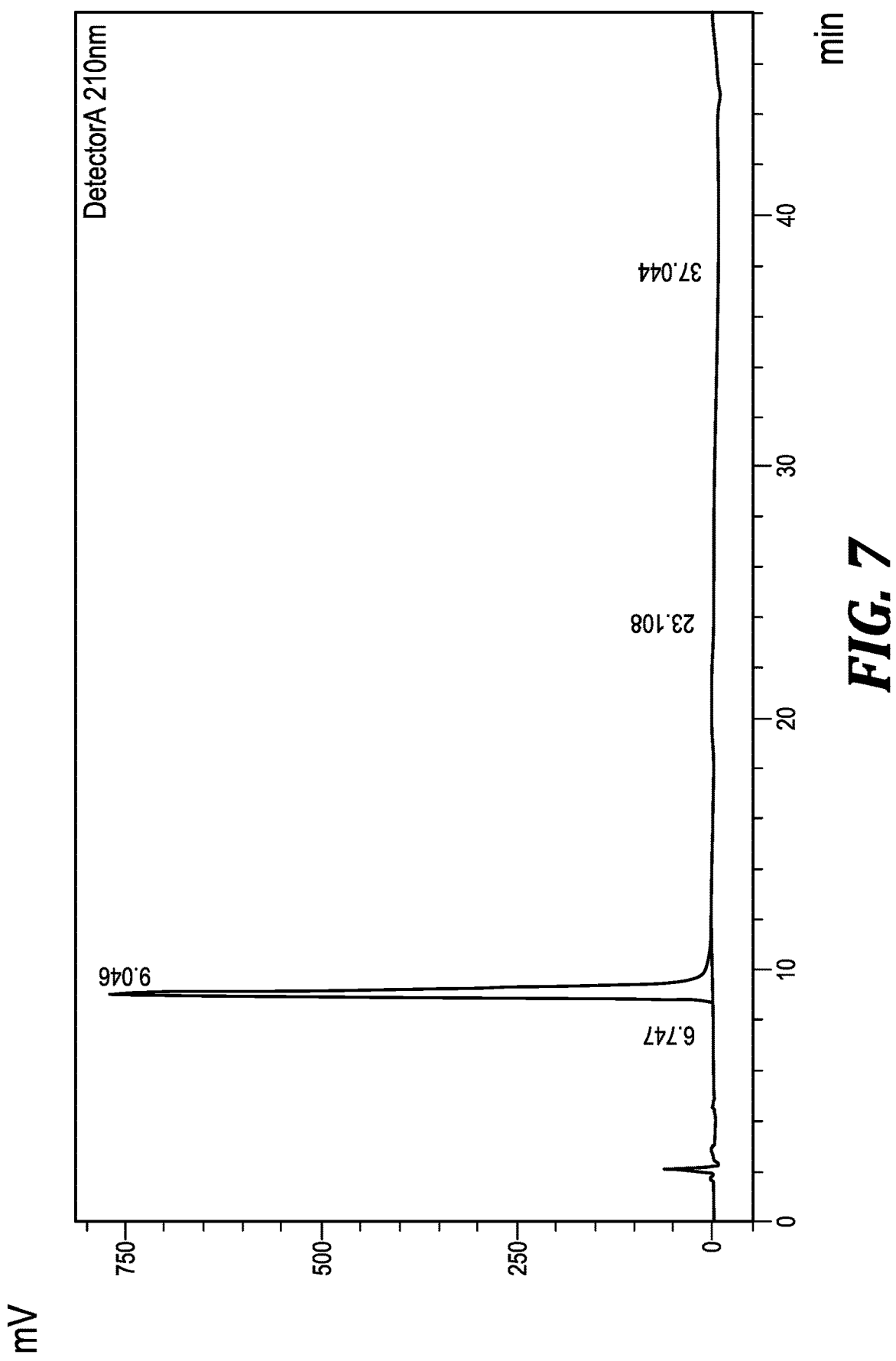
FIG. 7 shows the HPLC of Sitagliptin prepared under Condition 1 in Example 3.5 to determine the chemical purity of the product.
Figure 8:
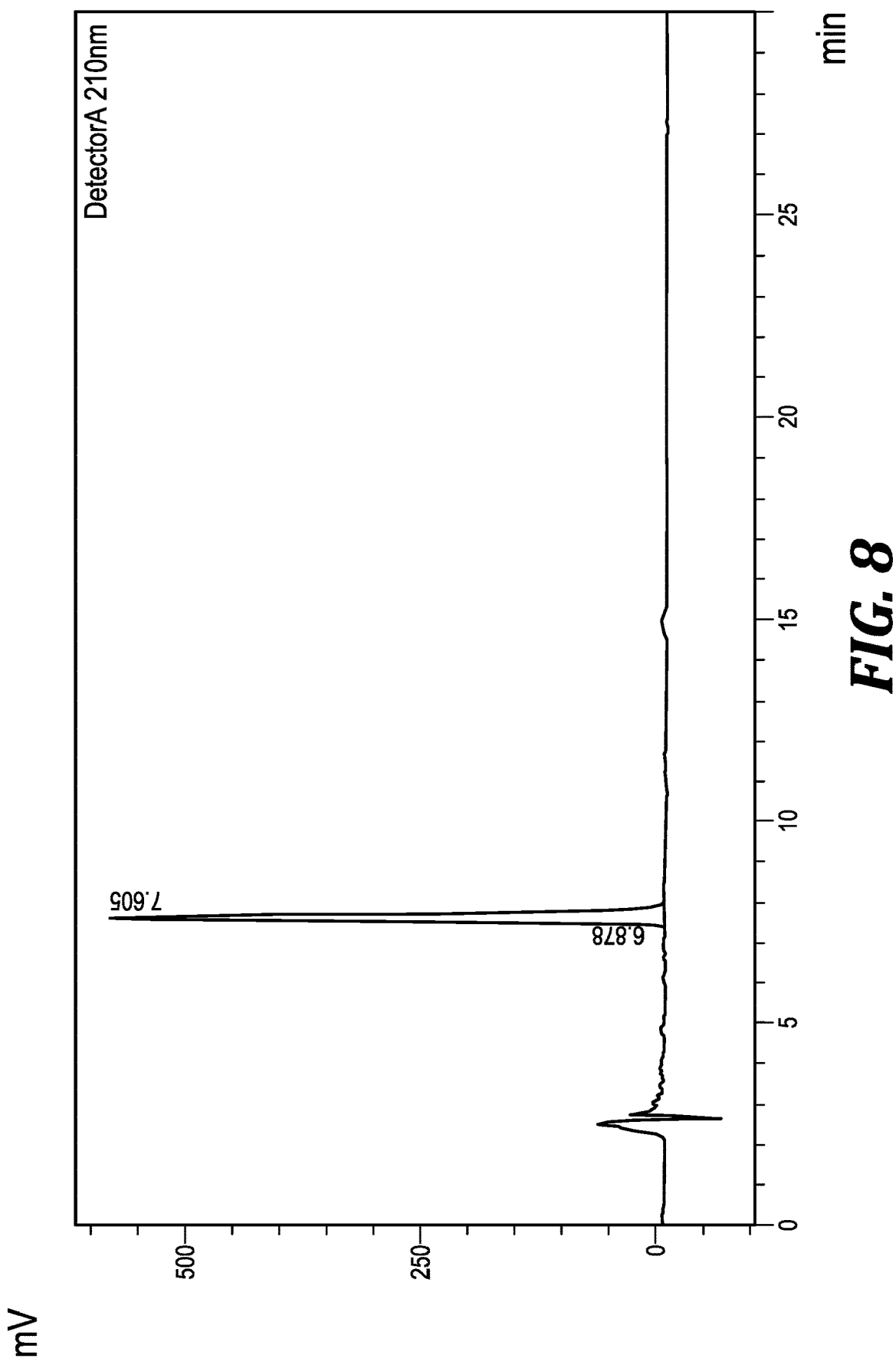
FIG. 8 shows the HPLC of Sitagliptin prepared under Condition 1 in Example 3.5 to determine the enantiomeric excess of the product.

5. Synthesis of Sitagliptin:

Condition 1:

To dichloromethane (300 ml), Compound IV (30 g) was added. The resultant mixture was cooled to 15° C. followed by an addition of thionyl chloride (26.8 g). The resultant mixture was heated to 25° C., and reacted for 2 h. Triethylamine (20 g) and 3-(trifluoromethyl)-5,6,7,8-tetrahydro-[1,2,4]triazolo[4,3-a]pyrazine hydrochloride (22.7 g) were added respectively. The resultant mixture was reacted at 25° C. for 5-6 h. Then water (100 ml) was added. The organic phase was separated, concentrated and crystallized, affording the dry product of Sitagliptin (34.8 g), with a purity of 99.8%, a chiral purity 99.9%, and a yield of 95%. The chemical purity and chiral purity of the product were determined by HPLC (as shown in FIG. 7 and FIG. 8 respectively).

Figure 9:
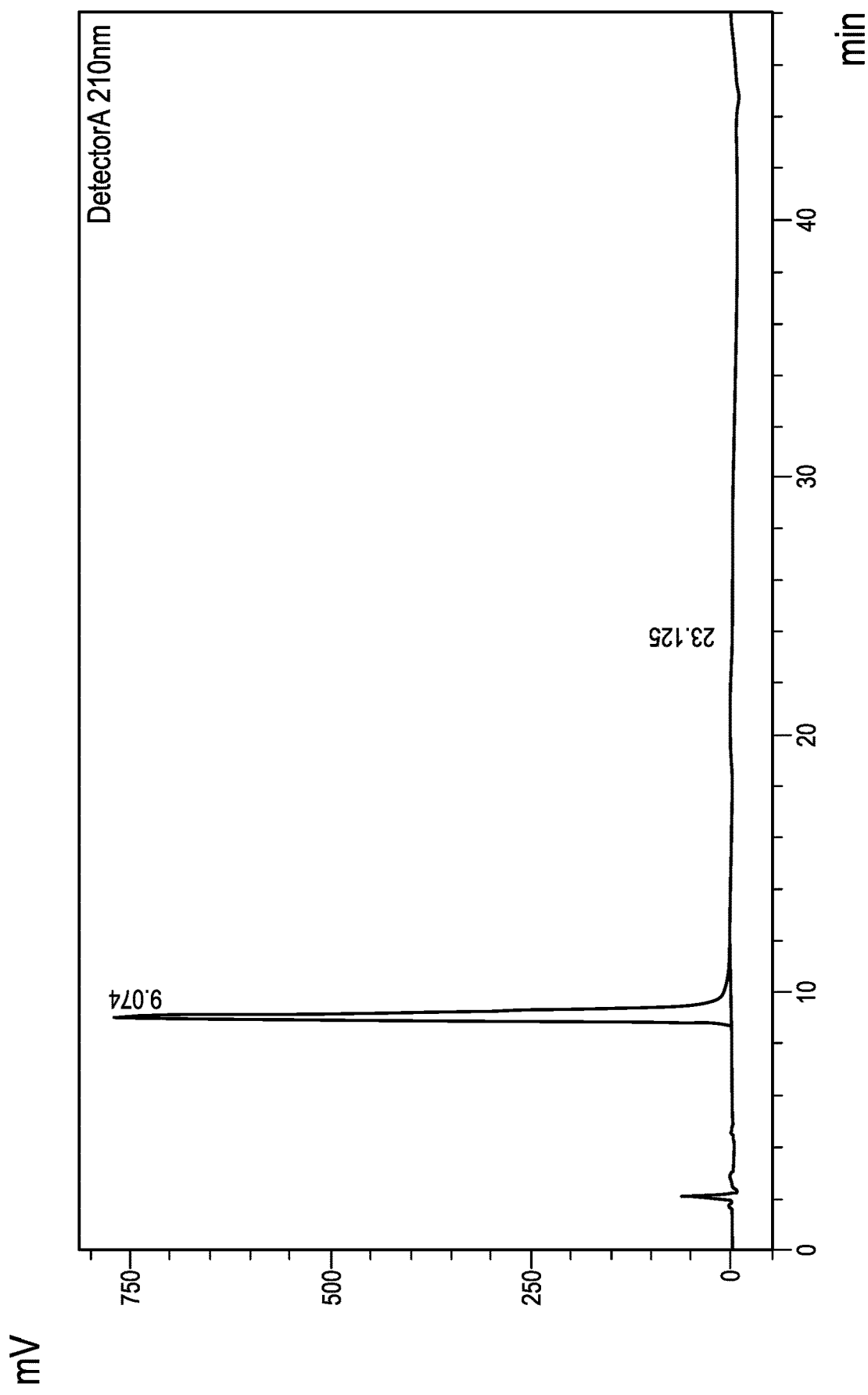
FIG. 9 shows the HPLC of Sitagliptin prepared under Condition 2 in Example 3.5 to determine the chemical purity of the product.
Figure 10:
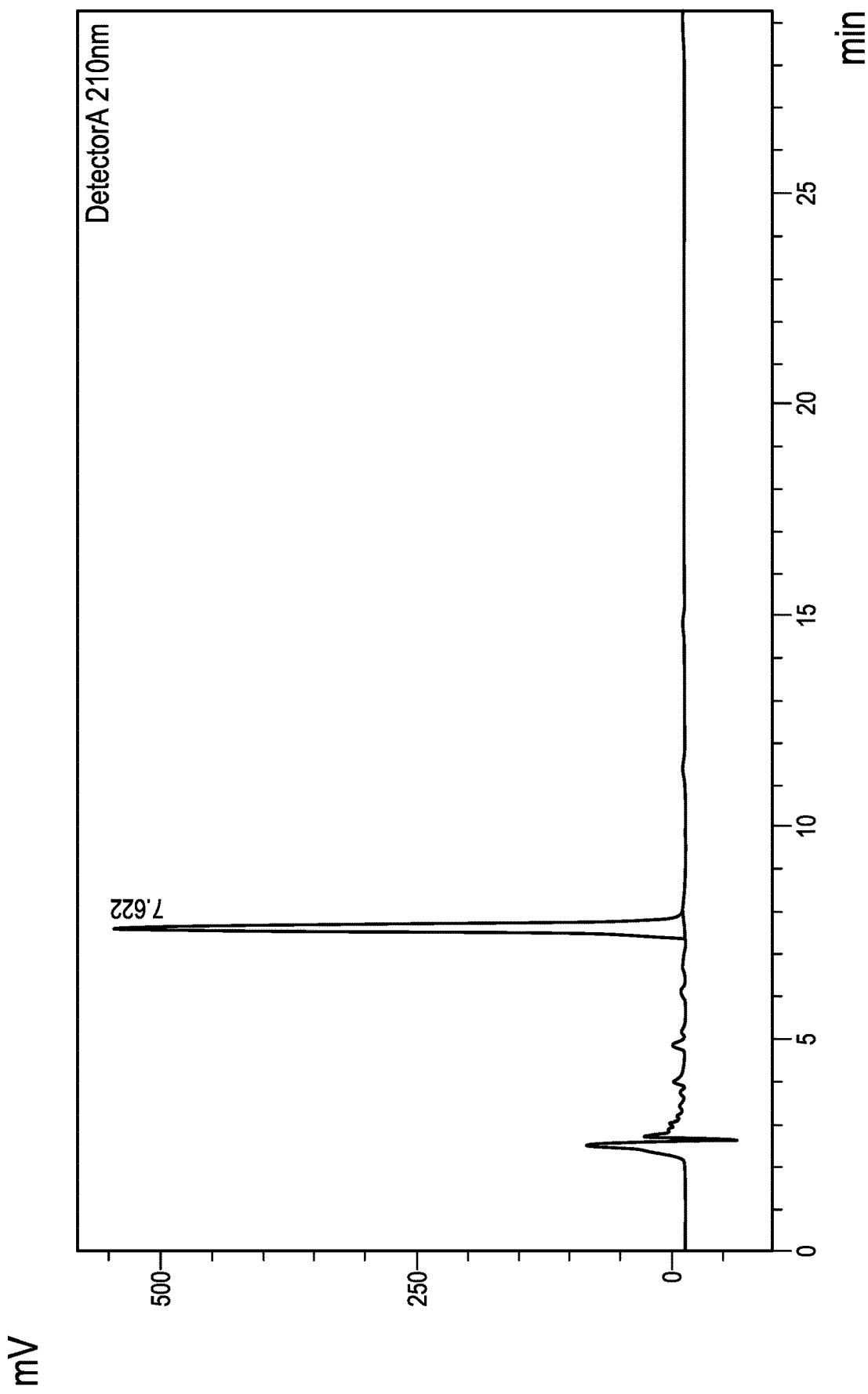
FIG. 10 shows the HPLC of Sitagliptin prepared under Condition 2 in Example 3.5 to determine the enantiomeric excess of the product.

Condition 2:

To ethyl acetate (250 ml), Compound V (30 g) was added. The resultant mixture was cooled to 15° C. followed by an addition of thionyl chloride (28 g). The resultant mixture was heated to 26° C., and reacted for 2 h. Triethylamine (23 g) and 3-(trifluoromethyl)-5,6,7,8-tetrahydro-[1,2,4]triazolo[4,3-a]pyrazine hydrochloride (223 g) were added respectively. The resultant mixture was reacted at 25° C. for 5-6 h. Then water (200 ml) was added. The organic phase was separated, concentrated and crystallized, affording the dry product of Sitagliptin (35.2 g), with a purity of 99.9%, a chiral purity of 100%, and a yield of 96%. The chemical purity and chiral purity of the product were determined by HPLC (as shown in FIG. 9 and FIG. 10 respectively).

Method for Determining Chiral Purity:

Chromatographic column: CHIRALPAK AD-H 4.6 mm×250 mm, 5 um;

Wavelength: 210 nm;

Column temperature: 40° C.;

Flow rate: 1.0 mL/min;

Sample volume: 20 uL;

Mobile phase: n-hexane:ethanol:isopropanol:diethylamine=400:500:100:3;

Diluent:methanol:mobile phase=50:50 (diluent was used to treat a sample and as a blank);

Method for Determining Chemical Purity:

Chromatographic column: Kromasil 100-5-C18 4.6 mm×250 mm, 5 um;

Flow rate: 1.0 ml/min;

Wavelength: 210 nm;

Sample volume: 20 ul;

Column temperature: 30° C.;

Preparation of Buffer:

9.6 g citric acid was dissolved in 1 L water, and 5% sodium hydroxide was used to adjust pH to 4, for further use.

Preparation of Mobile phase A: buffer:methanol=800:200, mixed, filtrated, and ultrasonically degassed for further use.

Preparation of Mobile phase B: methanol:tetrahydrofuran=900:100, mixed, filtrated, and ultrasonically degassed for further use.

Preparation of a diluent: methanol:water=50:50.

Program:

| Time (min) | A % | B % |
| --- | --- | --- |
| 0 | 90 | 10 |
| 15 | 60 | 40 |
| 20 | 90 | 10 |
| 50 | 90 | 10 |

Although the embodiments of the present invention have been described in detail, according to all the disclosed teachings, a person skilled in the art would understand that a variety of modifications and replacements may be performed to the details of the technical solutions of the present invention. These changes all fall into the protection scope of the invention. The whole scope of the present invention is defined by the attached claims and any equivalent thereof.

The invention claimed is:

1. A polypeptide having the activity of catalyzing the conversion of a carbonyl group to an amino group, wherein the polypeptide comprises the amino acid sequence as set forth in SEQ ID NO: 1.

2. An isolated nucleic acid, encoding the polypeptide according to claim 1.

3. A vector comprising the isolated nucleic acid according to claim 2.

4. A cell comprising the isolated nucleic acid according to claim 2 and/or a vector comprising the isolated nucleic acid, wherein, the isolated nucleic acid is heterogenous or exogenous for the cell.

5. A composition, comprising the polypeptide according to claim 1.

6. A method for producing a compound of Formula II or a pharmaceutically acceptable salt thereof, comprising the step of converting a compound of Formula I or a pharmaceutically acceptable salt thereof to the compound of Formula II or a pharmaceutically acceptable salt thereof by using the polypeptide according to claim 1 or a composition comprising the polypeptide, wherein, the chemical structures of Formula I and Formula II are as follows:

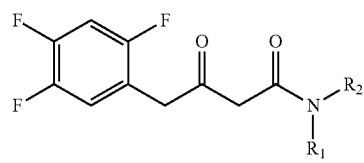

Formula I

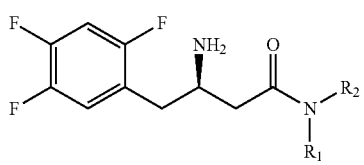

Formula II wherein, $R_1$ and $R_2$ are independently selected from the group consisting of hydrogen, $C_{1-6}$alkyl, 3-8-membered cycloalkyl, 3-8-membered heterocyclic alkyl, 6-10-membered aryl and 5-10-membered heteroaryl; or, $R_1$ and $R_2$ together with the N atom to which they are linked form a 4-7 membered heterocycle.

7. A method for synthesizing Sitagliptin or a salt thereof, comprising the following steps:

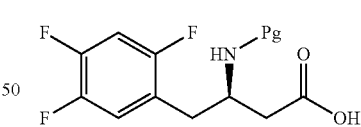

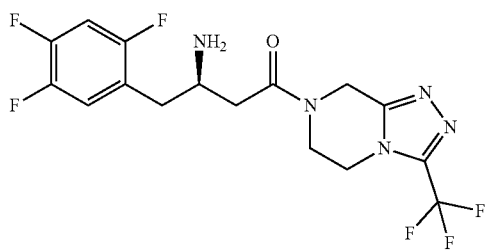

Sitagliptin the first step: the compound of Formula II is prepared according to the method of claim 6;

the second step: the compound of Formula II is hydrolyzed in the presence of a base to produce a compound of Formula III;

the third step: the amino group in the compound of Formula III is protected to produce a compound of Formula IV; and the fourth step: the compound of Formula IV and a compound of Formula V are subjected to condensation reaction, and the amino-protecting group of the product is removed, to produce Sitagliptin or a salt thereof;

wherein, -Pg represents an amino-protecting group;

$R_1$ and $R_2$ have the same meanings as defined in claim 6.

8. The method according to claim 7, characterized by one or more of the following items:

(1) the compound of Formula I is produced by the following method:

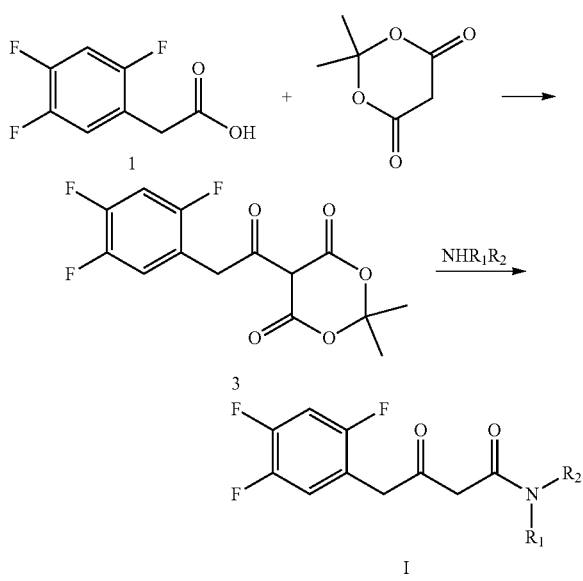

a) Compound 1 is reacted with Compound 2 in an aprotic solvent (e.g. EtOAc, DCM, DMF, DMA or DMSO; preferably DMA), in the presence of an organic base (e.g. methylamine, triethylamine, n-butyl amine or tert-butyl amine; preferably triethylamine), at room temperature or under heating (e.g. 20-50° C.; preferably 35° C.), to produce Compound 3; preferably, the molar ratio of Compound 1 and Compound 2 is 1: (1-5); preferably, after the reaction at room temperature or under heating, the step of adding an acidification agent is further comprised; more preferably, the acidification agent is selected from the group consisting of hydrochloric acid, thionyl chloride and pivaloyl chloride, and hydrochloric acid is preferred; preferably, the acidification agent is added in such an amount that the reaction system has an acidic pH;

b) Compound 3 and $NHR_1R_2$ in a non-alcohol solvent (e.g. benzene, toluene or tetrahydronaphthalene), are catalyzed by an inorganic base (e.g. sodium hydroxide or potassium hydroxide), under heating (e.g. 40-120° C.; e.g. 100-105° C.), to produce a compound of Formula I; preferably, the molar ratio of Compound 3 and $NHR1R_2$ is 1: (2-4);

(3) in the second step, the base is an inorganic base, e.g. sodium hydroxide or potassium hydroxide;

(4) in the third step, Boc anhydride reacts with a compound of Formula III in the presence of a base to protect the amino group; preferably, the molar ratio of the compound of Formula III, the Boc anhydride and the base is 1: (1.5-3): (2-4); preferably, the base is selected from the group consisting of sodium hydroxide, potassium hydroxide and triethylamine;

(5) in the fourth step, an active intermediate of the compound of Formula IV, and a compound of Formula V are subjected to condensation reaction; preferably, the active intermediate of the compound of Formula IV is an acyl chloride, an anhydride or an amide thereof; preferably, the molar ratio of the compound of Formula IV and the compound of Formula V is 1: (1-1.2); preferably, the condensation reaction is carried out in a non-alcohol solvent (e.g. ethyl acetate, dichloromethane or chloroform); preferably, the condensation reaction is carried out at room temperature (e.g. 25° C.); preferably, the condensation reaction is carried out in the presence of a base, more preferably, the base is triethylamine.

9. A method for preparing the polypeptide according to claim 1, comprising (a) culturing a host cell comprising and expressing a nucleic acid encoding the polypeptide, and (b) collecting the polypeptide expressed in the cell.

10. The method according to claim 6, comprising (a) reacting the compound of Formula I with an amino donor in the presence of the polypeptide or the composition and an amino transmitter; and (b) collecting the compound of Formula II produced in the step (a).

11. The method according to claim 10, in the step (a), $V(ml)_{the\ composition}$ : $m(g)_{the\ compound\ of\ Formula\ I}$ =(2-5): 1, the polypeptide is used in an amount of 10 wt. %-80 wt. % of the compound of Formula I.

12. The method according to claim 10, in the step (a), the amino donor is selected from $C_{1-6}$alkylamine, ammonium formate, ammonium chloride and ammonium sulfate, the molar ratio of the compound of Formula I to the amino donor is 1: (1-3).

13. The method according to claim 10, in the step (a), the amino donor is isopropyl amine, and the molar ratio of the compound of Formula I to the amino donor is 1: (1.2-3).

14. The method according to claim 10, in the step (a), the amino transmitter is selected from pyridoxal phosphate and pyridoxamine phosphate.

15. The method according to claim 10, in the step (a), the reaction is carried out in an aqueous phase.

16. The method according to claim 10, in the step (a), the compound of Formula I is dissolved in an alcohol solvent (e.g. methanol, ethanol or isopropanol) before being added to a reaction system (e.g. the compound of Formula I is dissolved in an alcohol solvent to form a 1-5 Kg/L solution, e.g. 1-4 Kg/L, e.g. 3-4 Kg/L), the concentration of the compound of Formula I is 100 g/L-250 g/L in the reaction system.

17. The method according to claim 10, in the step (a), the reaction is carried out at 30-50° C. (preferably 45° C.); the reaction system has a pH of 7.0-9.0 (preferably 8.0-9.0), and an organic amine (e.g. isopropyl amine, butyl amine or pentyl amine) is used to adjust pH of the reaction system.

18. The method according to claim 10, in the step (a), the reaction system is in contact with air.

19. The method according to claim 10, in the step (b), the compound of Formula II is collected by the following method: the product obtained in the step (a) is extracted with an organic solvent and concentrated, the organic solvent is selected from the group consisting of dichloromethane, ethyl acetate and isopropyl acetate.

* * * * *

SEQUENCE LISTING

<160> NUMBER OF SEQ ID NOS: 8

<210> SEQ ID NO 1
<211> LENGTH: 343
<212> TYPE: PRT
<213> ORGANISM: artificial
<220> FEATURE:
<223> OTHER INFORMATION: the amino acid sequence of Arthrobacter-derived transaminase mutant 1

<400> SEQUENCE: 1

```
Ser Val Leu His Arg Gly Gln Gln Arg Arg Phe His Ile Gln Phe
1               5                  10                  15

Pro Val Thr Thr Asp Asn Ala Leu Gly Asn Arg Thr Arg His Thr Val
                20                  25                  30

Arg Asn Gly Ile Thr Ile Asp Arg Asn Glu Arg Pro Asp Ala Thr Ala
            35                  40                  45

Gly Gly Ala Thr Gln Asn Phe Val Ser Ile Val Gln Phe Cys Arg Arg
    50                  55                  60

Asp Ile Gly Gln Asn Arg Phe Val Ala Gln Arg Phe Arg Asp Phe Gln
65                  70                  75                  80

Asn Gly Leu Ala Arg Asn Thr Arg Gln Ser Cys Thr Thr Arg Ala Thr
                85                  90                  95

Asn His Thr Ile Phe Asp Asp Asn His Ile Lys Ala Arg Thr Phe Ser
            100                 105                 110

Gln Gln Val Val Thr Ile Gln Gln Arg Gln Phe Glu Thr Ala Ile
    115                 120                 125

Met Gly Phe Leu Asp Cys Thr Asn Gln Val Ala Pro Leu Lys Val Leu
130                 135                 140

His Leu Arg Ile Asn Gly Thr Thr Arg Gly Ala Thr Asp Ala Leu Cys
145                 150                 155                 160

Asn His Gln Val His Thr Val Ala Asp Thr Ile Glu Arg Asn Asn Pro
                165                 170                 175

Leu Val Arg Ala Arg Thr His Ile His Leu Arg Ala Met Phe Gly Asp
            180                 185                 190

Ile Thr Phe Lys Arg Arg Ala Ile Ala Ala Gly Asn Arg His Gly
    195                 200                 205

Asp His Gly Phe Thr Gln Phe Gly Leu Gly His Gln Phe Gln Arg Asp
    210                 215                 220

Phe Phe Asp Phe Ile Leu Arg Gln Arg Asp Gln Ala Asn Arg Phe
225                 230                 235                 240

Cys Ile Ala Glu Gln Ala Phe Asn Val Val Ala Gln Thr Glu Ser Ile
                245                 250                 255

Thr Val Pro Asn Met Lys Arg Gly Val Gly Cys Val Arg Arg Ile Glu
            260                 265                 270

Thr Leu Ile Lys Asp Gly Asn Thr Gly Phe Thr Arg Arg His Lys Arg
    275                 280                 285

Thr Leu Asn Pro Cys Cys Thr Ala Ser Gln Arg Val Cys Arg Val Gln
    290                 295                 300

Phe Val Ala Val Gly Asn Val Val Gln Ala Arg Ile Val Gly Val
305                 310                 315                 320

Asn Asn Phe Arg Arg Val Cys Gly Glu Cys His Arg Ile Leu Ala Val
                325                 330                 335

Val Met Met Val Met Ala Ala
            340
```

<210> SEQ ID NO 2
<211> LENGTH: 972
<212> TYPE: DNA
<213> ORGANISM: artificial
<220> FEATURE:
<223> OTHER INFORMATION: the gene sequence of Arthrobacter-derived
transaminase mutant 1

<400> SEQUENCE: 2

| | |
|---|---|
| atggcctcta tggacaaagt cttttcggga tattatgcgc gccagaagct gcttgaacgg | 60 |
| agcgacaatc ctttctctaa gggcattgct tatgtggaag aaagctcgt ctttcctagt | 120 |
| gatgctagaa taccgctact cgacgaaggt ttcatgcaca gtgacctaac ctatgatgtt | 180 |
| atatcggttt gggatggtcg cttctttcga ttggacgatc atttgcaacg gattttggaa | 240 |
| agctgcgata gatgcggct caagttccca cttgcactga gcaccgtgga aaatattctg | 300 |
| gctgagatgg tcgccaagag tggtatccgg gatgcgtttg tggaagttat tgtgacacgt | 360 |
| ggtctgacag tgtacgtgg ttcgaagcct gaggatctgt ataataacaa catatacctg | 420 |
| cttgttcttc catacatttg ggttatggcg cctgagaacc agctccatgg tggcgaggct | 480 |
| atcattacaa ggacagtgcg acgaacaccc ccaggtgcat ttgatcctac tatcaaaaat | 540 |
| ctacagtggg gtgatttaac aaagggactt tttgaggcaa tggaccgtgg cgccacatac | 600 |
| ccatttctca ctgatggaga caccaacctt actgaaggat ctggtttcaa cattgttttg | 660 |
| gtgaagaacg gtattatcta tcccctgat cgaggtgtct tgcgagggat cacacgtaaa | 720 |
| agtgtgattg acgttgcccg agccaacagc atcgacatcc gccttgaggt cgtaccagtg | 780 |
| gagcaggctt atcactctga tgagatcttc atgtgcacaa ctgccggcgg cattatgcct | 840 |
| ataacattgc ttgatggtca acctgttaat gacggccagg ttggcccaat cacaaagaag | 900 |
| atatgggatg gctattggga gatgcactac aatccggcgt atagttttcc tgttgactat | 960 |
| ggcagtggct aa | 972 |

<210> SEQ ID NO 3
<211> LENGTH: 322
<212> TYPE: PRT
<213> ORGANISM: artificial
<220> FEATURE:
<223> OTHER INFORMATION: the amino acid sequence of Arthrobacter-derived
transaminase mutant 2

<400> SEQUENCE: 3

Ala Ala Ala Ile Thr Ile Ile Thr Thr Ala Arg Ile Arg Tyr Cys Thr
1               5                   10                  15

Gly Val Ser Arg Glu Glu Asp Ser Thr Phe Ser Ser Gln Gly Arg Arg
            20                  25                  30

Met Ile Asp Trp Val Thr Gly Pro Gly Thr Pro Ser Glu Ile Gly Leu
        35                  40                  45

Pro Ser Thr Glu Thr Asn Gly Gln Thr Pro Pro Val Val Gln Pro
    50                  55                  60

Arg Thr Ser Ser Ala Ser Ser Ser Ala Arg Val Met Ser Ala Arg
65                  70                  75                  80

Ile Ala Ser Gly Pro Arg Asp Ser Ala Ile Ser Arg Thr Val Leu Arg
                85                  90                  95

Val Ile Pro Gly Arg Ala Ala Ala Ser Arg Pro Ser Pro Ser Ser Ser
            100                 105                 110

Ser Gly Ala Ser Lys Pro Arg Ser Trp Val Ser Gly Thr Ala Arg Ile
        115                 120                 125

Arg Ser Pro His Trp Lys Phe Leu Thr Cys Gly Ser Ile Glu Glu Arg
130                 135                 140

Gly Val Arg Arg Thr Asp Gly Ala Thr Ile Ala Gly Thr Pro Ser Arg
145                 150                 155                 160

Met Arg Ser Asn Gly Thr Ile His Trp Tyr Gly Thr Ala Tyr Met Gly
            165                 170                 175

Thr Cys Gly Arg Cys Leu Val Met Ser Arg Ser Pro Gly Val Glu Glu
            180                 185                 190

Gly Pro Arg Val Ile Glu Thr Glu Thr Thr Ala Ser Arg Ser Ser Val
            195                 200                 205

Leu Ala Thr Ser Ser Arg Ala Ile Ser Leu Thr Ser Ser Trp Val Ser
210                 215                 220

Gly Gly Met Ile Arg Ile Asp Ser Ala Leu Glu Asn Arg Arg Ser Met
225                 230                 235                 240

Trp Ser Ser Arg Arg Lys Ala Leu Pro Phe Gln Thr Trp Asn Pro Val
                245                 250                 255

Gly Val Thr Ser Glu Cys Arg Gly Pro Trp Ser Lys Ile Glu Ile Arg
            260                 265                 270

Ala Ser Asp Gly Gly Thr Lys Ala Pro Ser Ile Gln Ala Ala Pro Pro
            275                 280                 285

Ala Ser Gly Leu Ala Gly Ser Ser Ser Gly Ser Glu Gly Val Ile Gly
290                 295                 300

Ser Arg Pro Val Ser Trp Val Gly Thr Ile Ser Glu Val Ser Ala Glu
305                 310                 315                 320

Lys Ala

<210> SEQ ID NO 4
<211> LENGTH: 968
<212> TYPE: DNA
<213> ORGANISM: artificial
<220> FEATURE:
<223> OTHER INFORMATION: the gene sequence of Arthrobacter-derived
      transaminase mutant 2

<400> SEQUENCE: 4
gcagcagcca tcaccatcat caccacagcc aggatccggt actgtaccgg ggtcagcaga      60
gaagaagatt caacgttcag ttcccagtaa cgacggatga tagactgggt aaccggaccc     120
ggaacaccgt cagagatcgg gttaccgtca acagaaacga acggccaaac accaccaccg     180
gtagtgcaac ccagaacttc gtcagcgtcc agcagttcag ccagggtgat gtcagccagg     240
atagcttcgt gacccagaga ttcagcgatt ccagaacgg ttttacgggt gatacccggc      300
agagcagcag ccagcagacc gtcaccgtcc agcagcagcg gagcttcgaa ccacggtcg      360 tgggtttcct gaactgcacg gatcaggtca ccccactgga agttttaac ctgcgggtcg      420 atagaagaac gcggagtacg acgaacagac tgagcaacca tagcgtgaac accgtcacgg     480
atgcggtcaa acggtacgat ccactggtac ggaacagcgt acatgtaaac ctgcggacga    540
tgtttggtga tgtcacgttc acctggggta gaagagtaac cacgggtgat agaaacagaa    600
acgactgctt cacgcagttc ggttttagca accagttcca gagcgatttc tttaacttcg    660
tcctgggtca gcggcgggat gatacgcata gattcagcgt tagagaacag acgttcgatg    720
tggtcgtcca gacggaaagc gttaccgttc caaacgtgga accgggtgta ggtaacgtca   780
gagtgcaggt aaccctggtc gaagatagag atacgagctt cagacggcgg aacgaaagca    840
ccttcgatcc aagcagcacc accagccagc gggttagccg ggtccagttc gtagtcagag    900

```
taggtgatat agtccagacc ggtgtcgtgg gtgtaaacga tttcagaggt gtcagcagag    960
aaagccat                                                              968
```

<210> SEQ ID NO 5
<211> LENGTH: 342
<212> TYPE: PRT
<213> ORGANISM: artificial
<220> FEATURE:
<223> OTHER INFORMATION: the amino acid sequence of Arthrobacter-derived transaminase mutant 3

<400> SEQUENCE: 5

| Ala | Ala | Ala | Ile | Thr | Ile | Ile | Thr | Thr | Ala | Arg | Ile | Arg | Tyr | Cys | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Val | Ser | Arg | Glu | Glu | Asp | Ser | Thr | Phe | Ser | Ser | Gln | Gly | Arg | Arg |
|     |     |     | 20  |     |     |     |     | 25  |     |     |     |     | 30  |     |     |

| Met | Ile | Asp | Trp | Val | Thr | Gly | Pro | Gly | Thr | Pro | Ser | Glu | Ile | Gly | Leu |
|     |     |     | 35  |     |     |     |     | 40  |     |     |     |     | 45  |     |     |

| Pro | Ser | Thr | Glu | Thr | Asn | Gly | Gln | Thr | Pro | Pro | Val | Glu | Gln | Pro |
|     | 50  |     |     |     |     | 55  |     |     |     |     | 60  |     |     |     |

| Arg | Thr | Ser | Ser | Ala | Ser | Ser | Ser | Ala | Arg | Val | Met | Ser | Ala | Arg |
| 65  |     |     |     |     | 70  |     |     |     |     | 75  |     |     |     | 80  |

| Ile | Ala | Ser | Gly | Pro | Arg | Asp | Ser | Ala | Ile | Ser | Arg | Thr | Val | Leu | Arg |
|     |     |     |     | 85  |     |     |     |     | 90  |     |     |     |     | 95  |     |

| Val | Ile | Pro | Gly | Arg | Ala | Ala | Arg | Pro | Gly | Glu | Arg | Thr | Thr | Pro | Ser |
|     |     |     | 100 |     |     |     |     | 105 |     |     |     |     | 110 |     |     |

| Leu | Ile | Thr | Thr | Thr | Leu | Lys | Pro | Gly | Pro | Ser | Ala | Ser | Arg | Pro | Ser |
|     |     |     | 115 |     |     |     |     | 120 |     |     |     |     | 125 |     |     |

| Pro | Ser | Ser | Ser | Gly | Ser | Ser | Lys | Pro | Arg | Ser | Trp | Val | Ser | Gly |
|     | 130 |     |     |     |     | 135 |     |     |     |     | 140 |     |     |     |

| Ile | Ala | Arg | Ile | Arg | Ser | Pro | His | Trp | Lys | Phe | Leu | Thr | Cys | Gly | Ser |
| 145 |     |     |     |     | 150 |     |     |     |     | 155 |     |     |     |     | 160 |

| Ile | Glu | Glu | Arg | Gly | Val | Arg | Arg | Thr | Asp | Gly | Ala | Thr | Ile | Ala | Gly |
|     |     |     |     | 165 |     |     |     |     | 170 |     |     |     |     | 175 |     |

| Thr | Pro | Ser | Arg | Met | Arg | Ser | Asn | Gly | Thr | Ile | His | Trp | Tyr | Gly | Thr |
|     |     |     |     | 180 |     |     |     |     | 185 |     |     |     |     | 190 |     |

| Ala | Tyr | Met | Gly | Thr | Cys | Gly | Arg | Cys | Leu | Val | Met | Ser | Arg | Ile | Tyr |
|     |     |     | 195 |     |     |     |     | 200 |     |     |     |     | 205 |     |     |

| Gly | Val | Glu | Glu | Gly | Pro | Arg | Val | Ile | Glu | Thr | Glu | Thr | Ile | Ala | Ser |
|     | 210 |     |     |     |     | 215 |     |     |     |     | 220 |     |     |     |     |

| Arg | Ser | Ser | Val | Leu | Ala | Thr | Ser | Ser | Arg | Ala | Ile | Ser | Leu | Thr | Ser |
| 225 |     |     |     |     | 230 |     |     |     |     | 235 |     |     |     |     | 240 |

| Ser | Trp | Val | Ser | Gly | Gly | Met | Ile | Arg | Ile | Asp | Ser | Ala | Leu | Glu | Asn |
|     |     |     |     | 245 |     |     |     |     | 250 |     |     |     |     | 255 |     |

| Arg | Arg | Ser | Met | Trp | Ser | Ser | Arg | Arg | Lys | Ala | Leu | Pro | Phe | Gln | Thr |
|     |     |     |     | 260 |     |     |     |     | 265 |     |     |     |     | 270 |     |

| Trp | Asn | Pro | Val | Gly | Val | Ala | Ser | Glu | Val | Arg | Gly | Pro | Trp | Ser | Lys |
|     |     |     | 275 |     |     |     |     | 280 |     |     |     |     | 285 |     |     |

| Ile | Glu | Ile | Arg | Ala | Ser | Asp | Gly | Gly | Thr | Lys | Ala | Pro | Ser | Ile | Gln |
|     | 290 |     |     |     |     | 295 |     |     |     |     | 300 |     |     |     |     |

| Ala | Ala | Pro | Pro | Ala | Ser | Gly | Leu | Ala | Gly | Ser | Ser | Trp | Ser | Glu |
| 305 |     |     |     |     | 310 |     |     |     |     | 315 |     |     |     | 320 |

| Gly | Val | Ile | Gly | Ser | Arg | Pro | Val | Ser | Trp | Val | Gly | Thr | Ile | Ser | Glu |
|     |     |     |     | 325 |     |     |     |     | 330 |     |     |     |     | 335 |     |

Val Ser Ala Glu Lys Ala
            340

<210> SEQ ID NO 6
<211> LENGTH: 1028
<212> TYPE: DNA
<213> ORGANISM: artificial
<220> FEATURE:
<223> OTHER INFORMATION: the gene sequence of Arthrobacter-derived
      transaminase mutant 3

<400> SEQUENCE: 6

```
gcagcagcca tcaccatcat caccacagcc aggatccggt actgtaccgg ggtcagcaga      60
gaagaagatt caacgttcag ttcccagtaa cgacggatga tagactgggt aaccggaccc     120
ggaacaccgt cagagatcgg gttaccgtca acagaaacga acggccaaac accaccaccg     180
gttgagcaac ccagaacttc gtcagcgtcc agcagttcag ccagggtgat gtcagccagg     240
atagcttcgt gacccagaga ttcagcgatt tccagaacgg ttttacgggt gatacccggc     300
agagcagcac gacccggaga acgaacaaca ccgtctttga taacaacaac gttgaaaccc     360
ggaccttcag ccagcagacc gtcaccgtcc agcagcagcg gcagctcgaa accacgggtcg    420
tgggtttcct gaattgcacg gatcaggtca ccccactgga agttttaac ctgcgggtcg      480
atagaagaac gcggagtacg acgaacagac tgagcaacca tagcgtgaac accgtcacgg     540
atgcggtcaa acggtacgat ccactggtac ggaacagcgt acatgtaaac ctgcggacga     600
tgtttggtga tgtcacgaat atatggggta gaagagtaac cacgggtgat agaaacagaa     660
acgattgctt cacgcagttc ggttttagca accagttcca gagcgatttc tttaacttcg     720
tcctgggtca gcggcgggat gatacgcata gattcagcgt tagagaacag acgttcgatg     780
tggtcgtcca gacggaaagc gttaccgttc caaacgtgga accggtgta ggtagcgtca      840
gaggtcaggt aaccctggtc gaagatagag atacgagctt cagacggcgg aacgaaagca     900
ccttcgatcc aagcagcacc accagccagc gggttagccg ggtccagttc gtggtcagag     960
taggtgatat agtccagacc ggtgtcgtgg gtgtaaacga tttcagaggt gtcagcagag    1020
aaagccat                                                             1028
```

<210> SEQ ID NO 7
<211> LENGTH: 342
<212> TYPE: PRT
<213> ORGANISM: artificial
<220> FEATURE:
<223> OTHER INFORMATION: the amino acid sequence of Arthrobacter-derived
      transaminase mutant 4

<400> SEQUENCE: 7

Ala Ala Ala Ile Thr Ile Ile Thr Thr Ala Arg Ile Arg Tyr Cys Thr
1               5                   10                  15

Gly Val Ser Arg Glu Glu Asp Ser Thr Phe Ser Ser Gln Gly Arg Arg
            20                  25                  30

Met Ile Asp Trp Val Thr Gly Pro Gly Thr Pro Ser Glu Ile Gly Leu
        35                  40                  45

Pro Ser Thr Glu Thr Asn Gly Gln Thr Pro Pro Val Glu Gln Pro
    50                  55                  60

Arg Thr Ser Ser Ala Ser Ser Ser Ala Arg Val Met Ser Ala Arg
65                  70                  75                  80

Ile Ala Ser Gly Pro Arg Asp Ser Ala Ile Ser Arg Thr Val Leu Arg
                85                  90                  95

```
Val Ile Pro Gly Arg Ala Ala Arg Pro Gly Glu Arg Thr Thr Pro Ser
                100                 105                 110

Leu Ile Thr Thr Thr Leu Lys Pro Gly Pro Ser Ala Ser Arg Pro Ser
            115                 120                 125

Gln Ser Ser Ser Gly Ser Ser Lys Pro Arg Ser Trp Val Ser Gly
    130                 135                 140

Ile Ala Arg Ile Arg Ser Pro His Trp Lys Phe Leu Thr Cys Gly Ser
145                 150                 155                 160

Ile Glu Glu Arg Gly Val Arg Arg Thr Asp Gly Ala Thr Ile Ala Gly
                165                 170                 175

Thr Pro Ser Arg Met Arg Ser Asn Gly Thr Ile His Trp Tyr Gly Thr
            180                 185                 190

Ala Tyr Met Gly Thr Cys Gly Arg Cys Leu Val Met Ser Arg Ser Asn
        195                 200                 205

Gly Val Glu Glu Gly Pro Arg Val Ile Glu Thr Glu Thr Ile Ala Ser
    210                 215                 220

Arg Ser Ser Val Leu Ala Thr Ser Ser Arg Ala Ile Ser Leu Thr Ser
225                 230                 235                 240

Ser Trp Val Ser Gly Gly Met Ile Arg Ile Asp Ser Ala Leu Glu Asn
                245                 250                 255

Arg Arg Ser Met Trp Ser Ser Arg Arg Lys Ala Leu Pro Phe Gln Thr
            260                 265                 270

Trp Lys Val Val Gly Val Ala Ser Glu Val Gly Pro Trp Ser Lys
        275                 280                 285

Ile Glu Ile Arg Ala Ser Asp Gly Gly Thr Lys Ala Pro Ser Ile Gln
290                 295                 300

Ala Ala Pro Pro Ala Ser Gly Leu Ala Gly Ser Ser Ser Gly Ser Glu
305                 310                 315                 320

Gly Val Ile Gly Ser Arg Pro Val Ser Trp Val Gly Thr Ile Ser Glu
                325                 330                 335

Val Ser Ala Glu Lys Ala
            340

<210> SEQ ID NO 8
<211> LENGTH: 1028
<212> TYPE: DNA
<213> ORGANISM: artificial
<220> FEATURE:
<223> OTHER INFORMATION: the gene sequence of Arthrobacter-derived
      transaminase mutant 4

<400> SEQUENCE: 8
gcagcagcca tcaccatcat caccacagcc aggatccggt actgtaccgg ggtcagcaga      60
gaagaagatt caacgttcag ttcccagtaa cgacggatga tagactgggt aaccggaccc     120
ggaacaccgt cagagatcgg gttaccgtca acagaaacga acggccaaac accaccaccg     180
gttgagcaac ccagaacttc gtcagcgtcc agcagttcag ccagggtgat gtcagccagg     240
atagcttcgt gacccagaga ttcagcgatt ccagaacgg ttttacgggt gatacccggc     300
agagcagcac gacccggaga acgaacaaca ccgtctttga taacaacaac gttgaaaccc     360
ggaccttcag ccagcagacc gtcgcagtcc agcagcagcg gcagctcgaa accacggtcg     420
tgggtttcct gaattgcacg gatcaggtca ccccactgga agtttttaac ctgcgggtcg     480
atagaagaac gcggagtacg acgaacagac tgagcaacca tagcgtgaac accgtcacgg     540
atgcggtcaa acggtacgat ccactggtac ggaacagcgt acatgtaaac ctgcggacga     600
```

```
tgtttggtga tgtcacgctc gaatggggta gaagagtaac cacgggtgat agaaacagaa    660
acgattgctt cacgcagttc ggttttagca accagttcca gagcgatctc tttaacttcg    720
tcctgggtca gcggcgggat gatacggata gattccgcgt tagagaacag acgttcgatg    780
tggtcgtcca gacggaaagc gttaccgttc caaacgtgga aggtggtgta ggtagcgtca    840
gaagtatagt aaccctggtc gaagatagag atacgagctt cagacggcgg aacgaaagca    900
ccttcgatcc aagcagcacc accagccagc gggttagccg ggtccagttc gtagtcagag    960
taggtgatat agtccagacc ggtgtcgtgg gtgtaaacga tttcagaggt gtcagctgag   1020
aaagccat                                                            1028
```

UNITED STATES PATENT AND TRADEMARK OFFICE
CERTIFICATE OF CORRECTION

PATENT NO. : 11,459,549 B2
APPLICATION NO. : 17/054135
DATED : October 4, 2022
INVENTOR(S) : F. Wu et al.

Page 1 of 1

It is certified that error appears in the above-identified patent and that said Letters Patent is hereby corrected as shown below:

In the Claims

| Column | Line | Claim | |
|--------|------|-------|---|
| 43 | 65 | 8 | change "R1" to -- $R_1$ --. |

Signed and Sealed this
Twentieth Day of February, 2024

*Katherine Kelly Vidal*

Katherine Kelly Vidal
*Director of the United States Patent and Trademark Office*